United States Patent
Hyde et al.

(10) Patent No.: US 9,445,728 B2
(45) Date of Patent: Sep. 20, 2016

(54) BLOOD PRESSURE CUFF

(71) Applicant: Elwha LLC, Bellevue, WA (US)

(72) Inventors: Roderick A. Hyde, Redmond, WA (US); Jordin T. Kare, Seattle, WA (US); Gary L. McKnight, Bothell, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 260 days.

(21) Appl. No.: 13/760,932

(22) Filed: Feb. 6, 2013

(65) Prior Publication Data

US 2013/0245390 A1    Sep. 19, 2013

Related U.S. Application Data

(63) Continuation-in-part of application No. 13/373,365, filed on Nov. 8, 2011, now Pat. No. 8,702,683, and a continuation-in-part of application No. 13/373,364, filed on Nov. 8, 2011, now Pat. No. 8,702,614.

(51) Int. Cl.
*A61B 5/0205* (2006.01)
*A61B 5/145* (2006.01)
*A61B 5/11* (2006.01)
(Continued)

(52) U.S. Cl.
CPC ............ *A61B 5/0205* (2013.01); *A61B 5/026* (2013.01); *A61B 5/02208* (2013.01); *A61B 5/1118* (2013.01); *A61B 5/14542* (2013.01); *A61B 5/6824* (2013.01); *A61B 5/6826* (2013.01); *A61B 5/6828* (2013.01); *A61B 5/6829* (2013.01); *A61B 5/6885* (2013.01); *A61B 5/7475* (2013.01); *A61B 2562/0219* (2013.01)

(58) Field of Classification Search
USPC .................. 600/301, 485, 490–499; 606/202
See application file for complete search history.

(56) References Cited

U.S. PATENT DOCUMENTS 3,095,873 A * 7/1963 Edmunds, Jr. ................ 600/499
3,143,111 A    8/1964 Green
(Continued)

FOREIGN PATENT DOCUMENTS

| WO | WO 98/26716 | 6/1998 |
| WO | WO 2007/033025 A2 | 3/2007 |
| WO | WO 2010/048528 A2 | 4/2010 |

OTHER PUBLICATIONS

PCT International Search Report; Application No. PCT/US12/64080; Jan. 25, 2013; pp. 1-2.
(Continued)

*Primary Examiner* — Kami A Bosworth
(74) *Attorney, Agent, or Firm* — Suiter Swantz pc llo

(57) ABSTRACT

A device can include a vibration sensor configured to sense blood flow in a lumen of a person; a cuff coupled to the vibration sensor and configured to contact a limb of the person; a mechanical cuff tensioner coupled to the cuff, the mechanical cuff tensioner configured to adjust a compressive force of the cuff on the lumen; a tension sensor operably coupled to the mechanical cuff tensioner, the tension sensor configured to measure a first tension value of the cuff during a first sense by the vibration sensor and to measure a second tension value of the cuff during a second sense by the vibration sensor; and a recorder mechanism configured to record the first tension value, the first measurement by the vibration sensor, the second tension value, and the second measurement by the vibration sensor.

50 Claims, 29 Drawing Sheets

(51) Int. Cl.
*A61B 5/00* (2006.01)
*A61B 5/026* (2006.01)
*A61B 5/022* (2006.01)

(56) References Cited

U.S. PATENT DOCUMENTS

| | | |
|---|---|---|
| 4,080,966 A | 3/1978 | McNally et al. |
| 4,280,494 A | 7/1981 | Cosgrove, Jr. et al. |
| 4,567,899 A | 2/1986 | Kamens et al. |
| 4,796,184 A | 1/1989 | Bahr et al. |
| 5,415,629 A | 5/1995 | Henley |
| 5,527,288 A | 6/1996 | Gross et al. |
| 5,848,991 A | 12/1998 | Gross et al. |
| 5,997,501 A | 12/1999 | Gross et al. |
| 6,251,080 B1 | 6/2001 | Henkin et al. |
| 6,723,077 B2 | 4/2004 | Pickup et al. |
| 7,207,944 B2 | 4/2007 | Fumuro et al. |
| 7,267,665 B2 | 9/2007 | Steil et al. |
| 7,392,080 B2 | 6/2008 | Eppstein et al. |
| 7,481,772 B2 | 1/2009 | Banet |
| 7,544,190 B2 | 6/2009 | Pickup et al. |
| 7,628,759 B2 | 12/2009 | Freund et al. |
| 7,717,855 B2 * | 5/2010 | Caldarone et al. ........... 600/496 |
| 7,963,921 B1 | 6/2011 | Freund et al. |
| 8,182,429 B2 | 5/2012 | Mason |
| 8,197,416 B1 | 6/2012 | Shankar |
| 8,319,401 B2 | 11/2012 | McKenna |
| 2002/0016610 A1 * | 2/2002 | Hovanes et al. ............... 606/203 |
| 2002/0017296 A1 | 2/2002 | Hickle |
| 2002/0038101 A1 | 3/2002 | Avrahami et al. |
| 2002/0042635 A1 | 4/2002 | Zhang et al. |
| 2003/0004403 A1 | 1/2003 | Drinan et al. |
| 2003/0065294 A1 | 4/2003 | Pickup et al. |
| 2004/0087916 A1 | 5/2004 | Pickup et al. |
| 2004/0167409 A1 | 8/2004 | Lo et al. |
| 2004/0181196 A1 | 9/2004 | Pickup et al. |
| 2005/0131310 A1 | 6/2005 | Freund et al. |
| 2005/0148882 A1 | 7/2005 | Banet et al. |
| 2005/0182389 A1 | 8/2005 | LaPorte et al. |
| 2005/0187485 A1 | 8/2005 | Fumuro et al. |
| 2005/0288597 A1 * | 12/2005 | Kishimoto et al. ........... 600/499 |
| 2006/0100530 A1 | 5/2006 | Kliot et al. |
| 2006/0217617 A1 | 9/2006 | Wachtenberg |
| 2006/0253041 A1 * | 11/2006 | Shin et al. .................... 600/493 |
| 2007/0191702 A1 | 8/2007 | Yodfat et al. |
| 2007/0265533 A1 | 11/2007 | Tran |
| 2009/0076349 A1 | 3/2009 | Libbus et al. |
| 2009/0187167 A1 | 7/2009 | Sexton et al. |
| 2010/0030111 A1 | 2/2010 | Perriere |
| 2010/0106030 A1 * | 4/2010 | Mason ......................... 600/493 |
| 2010/0234716 A1 | 9/2010 | Engel |
| 2011/0092898 A1 | 4/2011 | Chuang |
| 2011/0264028 A1 | 10/2011 | Ramdas et al. |
| 2012/0059267 A1 | 3/2012 | Lamego et al. |
| 2013/0211267 A1 | 8/2013 | Wang et al. |

OTHER PUBLICATIONS

PCT International Search Report; International App. No. PCT/US12/64071; Jan. 17, 2013; pp. 1-2 (including 6 pages of the Search Report).

"Hypertension"; Wikipedia, the free encyclopedia; printed on Nov. 7, 2011; http://en.wikipedia.org/wiki/High_blood_pressure; pp. 1-22.

"Systolic Hypertension"; Wikipedia, the free encyclopedia; printed on Nov. 7, 2011; http://en.wikipedia.org/wiki/Systolic_hypertension; pp. 1-4.

Benjamin J. Powers et al., Measuring Blood Pressure for Decision Making and Quality Reporting: Where and How Many Measures?, Annals of Internal Medicine, Jun. 21, 2011, vol. 154, No. 12, © 2011 American College of Physicians, pp. 781-788.

Lawrence J. Appel, et al., Improving the Measurement of Blood Pressure: Is It Time for Regulated Standards?, Annals of Internal Medicine, Jun. 21, 2011, vol. 154, No. 12, © 2011 American College of Physicians, pp. 838-839.

Infinity® CNAP™ (Continuous Noninvasive Arterial Pressure) SmartPod®, http://www.draeger.com/sites/en_uk/pages/hospital/infinity-cnap-smartpod.aspx, 1 page, Printed on May 28, 2013.

Withings Smart Blood Pressure Monitor (for iPhone, iPad, and iPod Touch), http://www.amazon.com/Withings-Smart-Pressure-Monitor-iPhone/dp/B004K2KYM8/ref, pp. 1-6, Printed on May 28, 2013.

Withing Blood Pressure Monitor for iOS Devices—YouTube, http://www.youtube.com/watch?v=CpnUxz4LLCM, pp. 1-2, Printed on May 28, 2013.

Biopac Systems, Inc., NIBP100D Noninvasive Blood Pressure Monitoring System, Product Sheet, May 21, 2013, p. 1-3.

PCT International Search Report; International App. No. PCT/US2014/015018; May 19, 2014; pp. 1-3.

Extended European Search Report; European App. No. EP 12 84 7228; Mar. 26, 2015; pp. 1-7.

Extended European Search Report; European App. No. EP 12 84 6846; Mar. 19, 2015; pp. 1-8.

* cited by examiner

BLOOD PRESSURE CUFF

CROSS-REFERENCE TO RELATED APPLICATIONS

The present application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)). In addition, the present application is related to the "Related Applications," if any, listed below.

PRIORITY APPLICATIONS

For purposes of the USPTO extra-statutory requirements, the present application constitutes a continuation-in-part of U.S. patent application Ser. No. 13/373,365, entitled SYSTEMS AND METHODS FOR DYNAMIC DRUG THERAPY RESPONSE TO BLOOD PRESSURE INCIDENTS, naming Michael H. Baym, Edward S. Boyden, Roderick A. Hyde, Jordin T. Kare, Eric C. Leuthardt, Nathan P. Myhrvold, and Lowell L. Wood, Jr. as inventors, filed Nov. 8, 2011, which is currently co-pending or is an application of which a currently co-pending application is entitled to the benefit of the filing date.

For purposes of the USPTO extra-statutory requirements, the present application constitutes a continuation-in-part of U.S. patent application Ser. No. 13/373,364, entitled INFLATABLE CUFF WITH BUILT-IN DRUG DELIVERY DEVICE FOR DYNAMIC DRUG THERAPY RESPONSE TO BLOOD PRESSURE INCIDENTS, naming Michael H. Baym, Edward S. Boyden, Roderick A. Hyde, Jordin T. Kare, Eric C. Leuthardt, Nathan P. Myhrvold, and Lowell L. Wood, Jr. as inventors, filed Nov. 8, 2011, which is currently co-pending or is an application of which a currently co-pending application is entitled to the benefit of the filing date.

RELATED APPLICATIONS

U.S. patent application Ser. No. 13/760,939, titled BLOOD PRESSURE CUFF, naming Roderick A. Hyde, Jordin T. Kare, Gary L. McKnight, and Lowell L. Wood, Jr. as inventors, filed Feb. 6, 2013, is related to the present application.

If an Application Data Sheet (ADS) has been filed on the filing date of this application, it is incorporated by reference herein. Any applications claimed on the ADS for priority under 35 U.S.C. §§119, 120, 121, or 365 (c), and any and all parent, grandparent, great-grandparent, etc. applications of such applications, are also incorporated by reference, including any priority claims made in those applications and any material incorporated by reference, to the extent such subject matter is not inconsistent herewith.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, *Benefit of Prior-Filed Application*, USPTO Official Gazette Mar. 18, 2003. The USPTO further has provided forms for the Application Data Sheet which allow automatic loading of bibliographic data but which require identification of each application as a continuation, continuation-in-part, or divisional of a parent application. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above and in any ADS filed in this application, but expressly points out that such designation(s) are not to be construed in any way as any type of commentary and/or admission as to whether or not the present application contains any new matter in addition to the matter of its parent application(s).

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

SUMMARY

A device may include a vibration sensor configured to sense blood flow in a lumen of a person; a cuff coupled to the vibration sensor and configured to contact a limb of the person; a mechanical cuff tensioner coupled to the cuff, the mechanical cuff tensioner configured to adjust a compressive force of the cuff on the lumen; a tension sensor operably coupled to the mechanical cuff tensioner, the tension sensor configured to measure a first tension value of the cuff during a first sense by the vibration sensor and to measure a second tension value of the cuff during a second sense by the vibration sensor; and a recorder mechanism configured to record the first tension value, the first measurement by the vibration sensor, the second tension value, and the second measurement by the vibration sensor.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
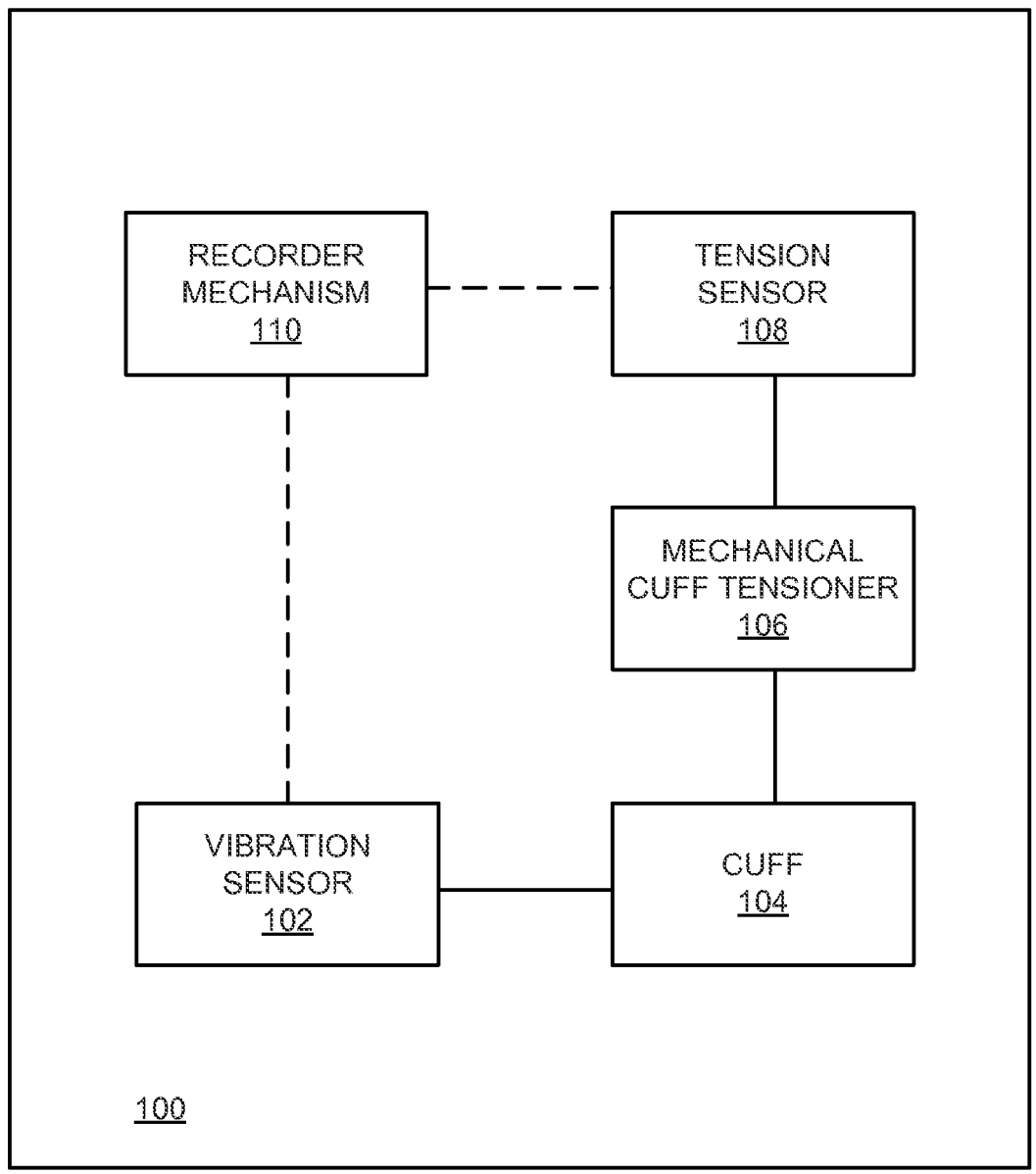
FIG. 1 is a schematic of a blood pressure cuff.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

Referring now to FIGS. 1-17, a blood pressure cuff 100 is described in accordance with the present disclosure. The blood pressure cuff 100 can generally include a vibration sensor 102, a cuff 104, a mechanical cuff tensioner 106, a tension sensor 108, and a recorder mechanism 110. The blood pressure cuff 100 can be configured to contact a limb of human or animal and to measure or derive a blood pressure of blood within a lumen of the human or animal. The limb can include an arm, a leg, a finger, or a toe of the human or animal.

In an embodiment, illustrated in FIG. 1, the blood pressure cuff 100 includes a vibration sensor 102 configured to sense blood flow in a lumen of a human or animal, such as through proximity of the vibration sensor 102 relative to such lumen. The vibration sensor 102 can be an acoustic sensor, a piezoelectric sensor, or other sensor suitable to sense vibrations of blood flow in a lumen of the human or animal. The blood pressure cuff 100 also includes a cuff 104 coupled to the vibration sensor 102 and configured to removably contact the limb of the human or animal. The cuff 104 can be configured for contacting the limb of the human or animal to secure the blood pressure cuff 100 in place for a duration sufficient for the vibration sensor 102 to sense the blood flow in the lumen. The blood pressure cuff 100 also includes a mechanical cuff tensioner 106 coupled to the cuff 104. The mechanical cuff tensioner 106 is configured to adjust a compressive force of the cuff 104 on the lumen. For instance, the mechanical cuff tensioner 106 is configured to tension and de-tension the cuff 104 about the limb. The mechanical cuff tensioner 106 and the cuff 104 can act in conjunction to secure the blood pressure cuff 100 in place for a duration sufficient for the vibration sensor 102 to sense the blood flow in the lumen, which can include a plurality of sensed blood flow characteristics. The blood pressure cuff 100 also includes a tension sensor 108 operably coupled to the mechanical cuff tensioner 106. The tension sensor 108 is configured to measure a first tension value of the cuff 104 during a first sense by the vibration sensor 102 and to measure a second tension value of the cuff 104 during a second sense by the vibration sensor 102. The blood pressure cuff 100 also includes a recorder mechanism 110, which can be operably coupled to the vibration sensor 102 and the tension sensor 108. The recorder mechanism 110 is configured to record the first tension value (e.g., from the tension sensor 108), the first measurement by the vibration sensor 102, the second tension value (e.g., from the tension sensor 108), and the second measurement by the vibration sensor 102. The recorder mechanism 110 can include one or more of a data storage medium, an addressing logic for memory storage, and memory management logic for the storage of data. The vibration sensor 102 and the tension sensor 108 can be configured to activate simultaneously, such that the first measurement by the vibration sensor 102 is taken at the same time as the first tension value by the tension sensor 108, or they may be configured to act sequentially.

One or more of the vibration sensor 102 and the tension sensor 108 can operate periodically or continuously, where vibration measurements and tension measurements are taken periodically or continuously, respectively. In an embodiment, the first measurement by the vibration sensor 102 can be at a systolic phase of the blood flow through the lumen and the second measurement by the vibration sensor 102 can be at a diastolic phase of the blood flow through the lumen.

Figure 2:
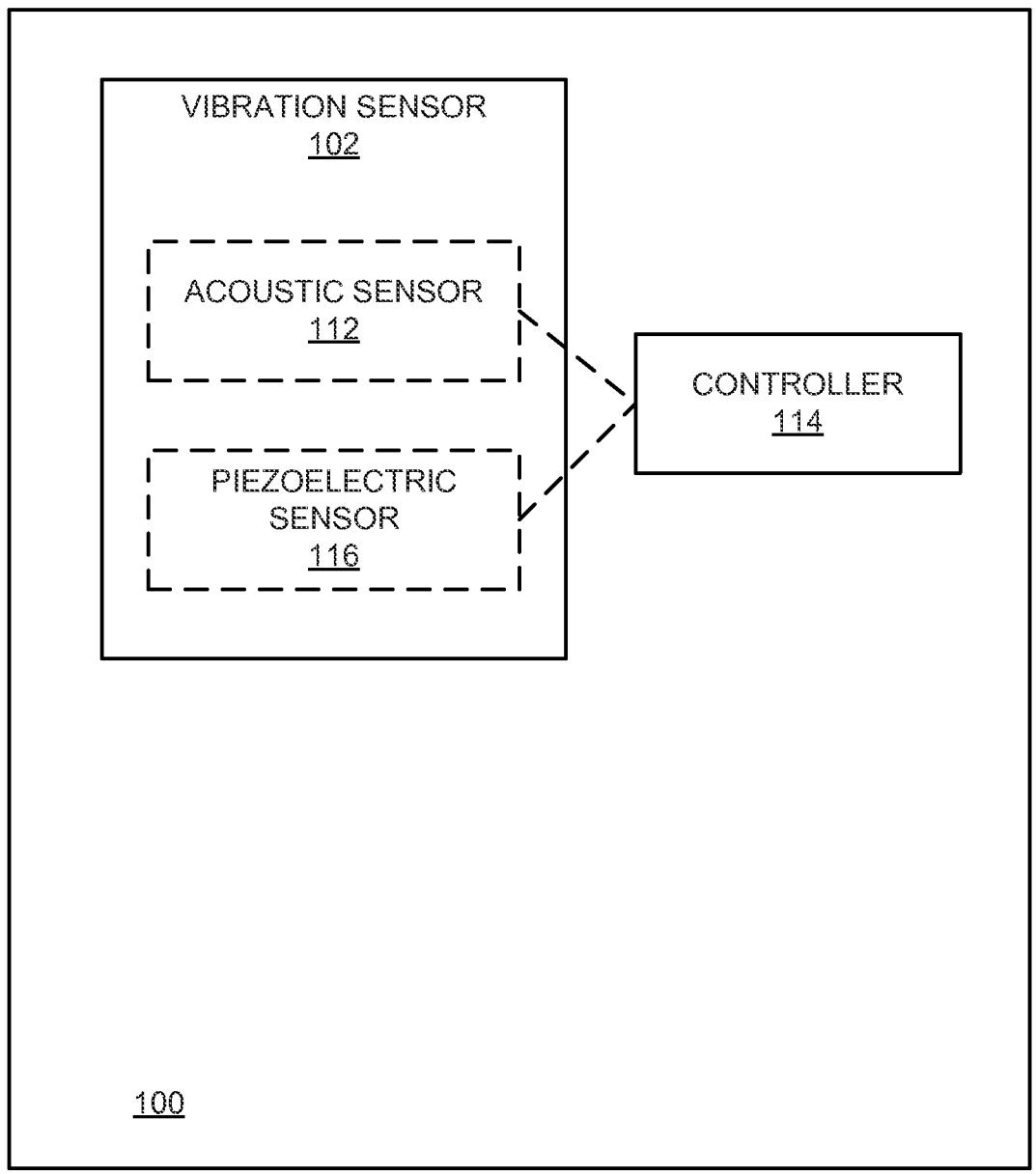
FIG. 2 is a schematic of an alternative embodiment of a blood pressure cuff.

In an embodiment, illustrated in FIG. 2, the vibration sensor 102 of the blood pressure cuff 100 can include an acoustic sensor 112. The blood pressure cuff 100 can also include a controller 114 operably coupled to the acoustic sensor 112. The controller 114 includes circuitry to determine a sound indicative of at least one systole and diastole based on at least one of the first measurement or the second measurement of the vibration sensor 102. For example, the controller circuitry can determine a Korotkoff sound. The vibration sensor 102 can also or alternatively include a piezoelectric sensor 116. The controller 114 can be operably coupled to the piezoelectric sensor 116 and can include circuitry to determine at least one vibration pattern indicative of systole and diastole based on at least one of the first measurement or the second measurement of the vibration sensor 102. Such determinations of a Korotkoff sound indicative of at least one systole and diastole and of at least one vibration pattern indicative of systole and diastole can be utilized to correlate the systolic blood pressure and the diastolic blood pressure of the blood flow through the lumen of the human or animal.

Figure 3:
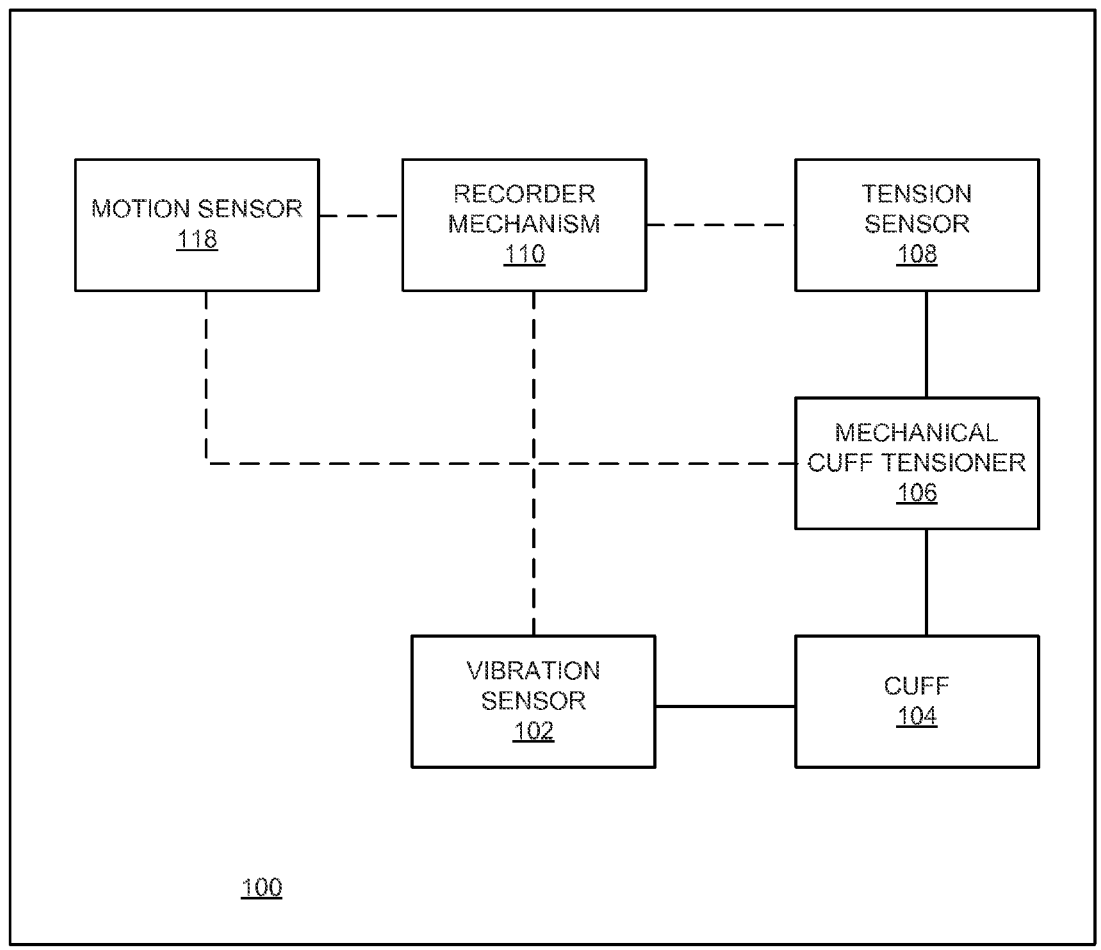
FIG. 3 is a schematic of an alternative embodiment of a blood pressure cuff.

In an embodiment, illustrated in FIG. 3, the blood pressure cuff 100 includes a motion sensor 118 operably coupled to the recorder mechanism 110 or to the controller 114. The motion sensor 118 can include an accelerometer, for example. The motion sensor 118 can be configured to detect a motion of the cuff 104. For instance, the motion sensor 118 can be configured to detect a lateral motion of the cuff 104 signifying a tightening or loosening of the cuff 104 relative to the limb of the human or animal. The motion sensor 118 may operate to command an increase of the "resting" tension (i.e., that between measurement events) when the sensed motion exceeds a threshold, such as when the cuff 104 has moved substantially away from the limb, in order to keep cuff 104 snug against the limb. The motion sensor 118 can operate to avoid unnecessary operation of the tension sensor 108 by disabling the tension sensor 106 when the sensed motion exceeds a threshold, such as when the cuff 104 has moved substantially away from the limb (e.g., loosened from contact with the limb).

Figure 4:
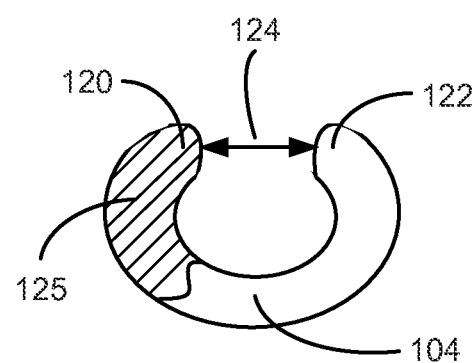
FIG. 4 is a schematic of an alternative embodiment of a blood pressure cuff.

In some embodiments, the length of the cuff 104 is configured to extend partially, substantially, or totally around the circumference of the limb. As shown in the embodiment of FIG. 4, the cuff 104 includes a first end 120 and a second end 122, with a gap 124 defined between the first end 120 and the second end 122. For partial or substantial extension around the circumference of the limb, the length of the gap 124 can be approximately 5, 10, 15, 20, 25 or more percent of the length of the cuff 104, although other ranges can be suitable. The cuff 104 can also include a flexible sleeve 125, at least a portion of which is positioned on an exterior of the cuff 104. The flexible sleeve 125 can be constructed from protective or thermally insulating materials to protect one or more of the blood pressure cuff 100 or the individual using the blood pressure cuff 100.

Figure 5:
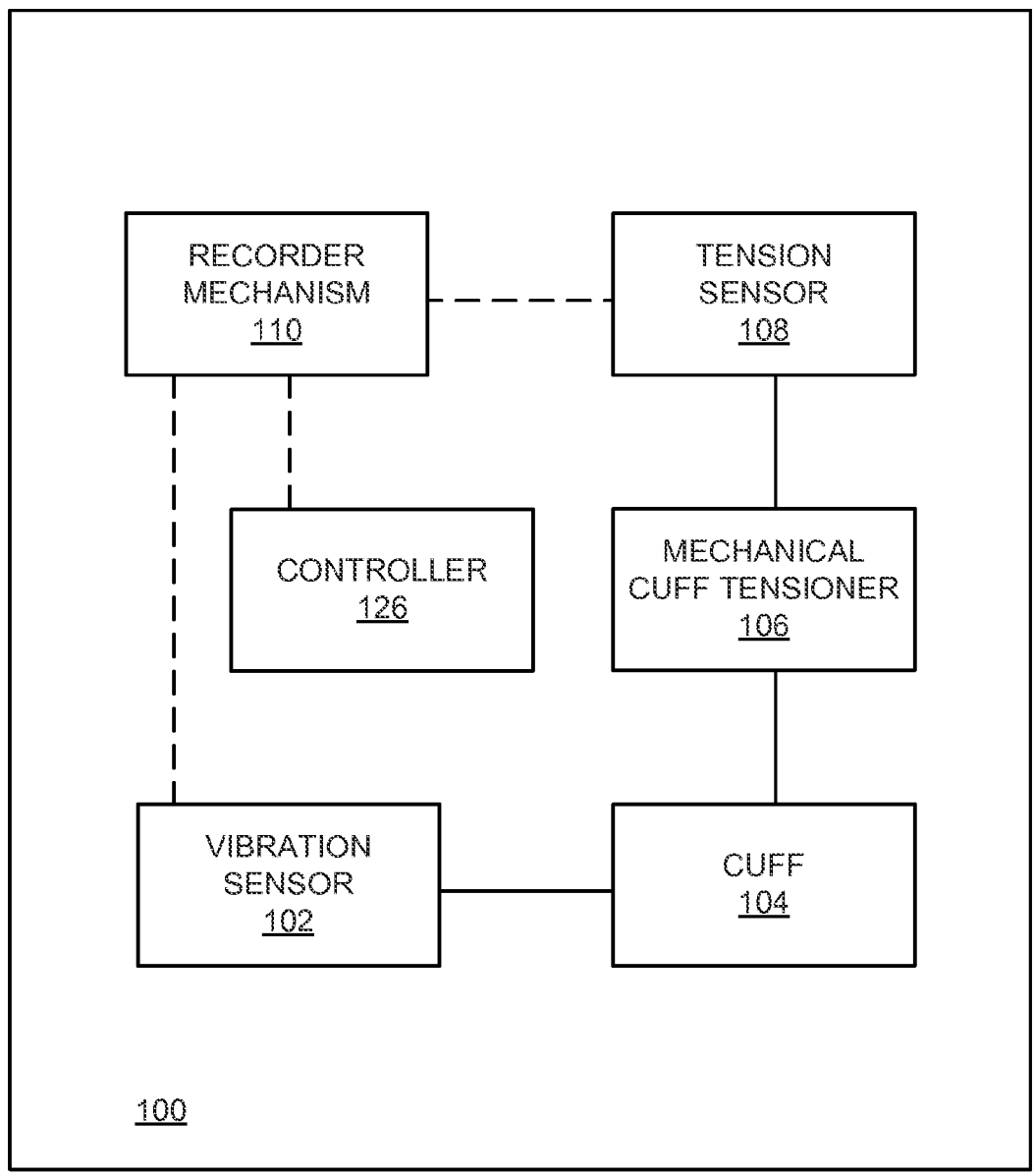
FIG. 5 is a schematic of an alternative embodiment of a blood pressure cuff.

In an embodiment, illustrated in FIG. 5, the blood pressure cuff 100 includes a controller 126 configured to calculate at least one of a systolic blood pressure or a diastolic blood pressure of blood in the lumen based on the first tension value, the second tension value, and a circumference of the cuff 104. The controller 126 can include a processor, microprocessor, or other device suitable for performing calculations. The controller 126 may include or may be operably coupled to a memory for storing one or more values used for calculations. The controller 126 can calculate the pressure applied by blood pressure cuff 100 to the limb by use of a relation such as $P=KT/(RW)$ Where P represents blood pressure (systolic pressure when T is the first tension value, and diastolic pressure when T is the second tension value), T the cuff tension, R the average limb radius, and W a lateral dimension of the cuff, wherein K represents a correction value depending upon details such as the limb eccentricity, cross-sectional shape of the cuff, etc. In some embodiments the limb radius and eccentricity can be known based on previous deployment of the cuff 104 to a specified limb location; in such embodiments, pressure can be related to cuff tension by a proportionality constant. In some embodiments, the limb radius can be determined from cuff-based limb circumference measurements and with limb-based eccentricity values. In some embodiments, the lateral dimension of the cuff can be the physical width or the average width if the physical width varies along the cuff. In some embodiments, only a portion of the physical width is effective at applying force to the limb, in such cases this effective width can be used rather than the physical width.

The controller 126 can be operably coupled to the recorder mechanism 110 to access data associated with one or more of the first tension value, the second tension value, the circumference of the cuff 104, the limb radius, the lateral dimension of the cuff, and the correction value. By utilizing the tension values associated with the mechanical cuff tensioner 106 and the cuff 104, the controller 126 can account for varying sizes of limbs of differing individuals using the blood pressure cuff 100. The controller 126 also can be configured to calculate at least one of a systolic blood pressure or a diastolic blood pressure based on the first tension value, the second tension value, and a lateral dimension of the cuff 104. The controller 126 further can be configured to calculate at least one of a systolic blood pressure or a diastolic blood pressure based on the first tension value, the second tension value, and an eccentricity factor of the cuff 104.

Figure 6:
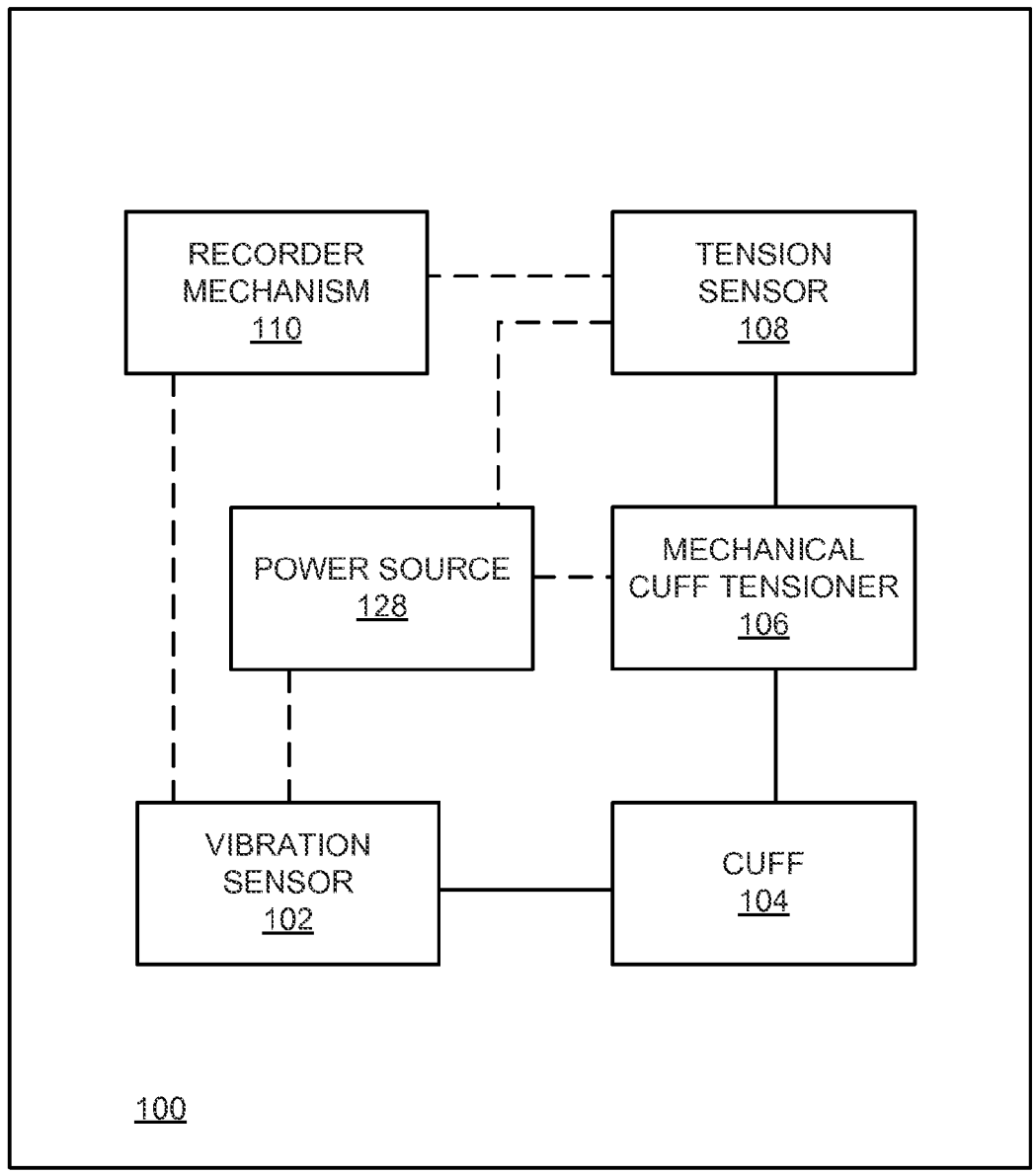
FIG. 6 is a schematic of an alternative embodiment of a blood pressure cuff.

In an embodiment, illustrated in FIG. 6, the blood pressure cuff 100 includes a power source 128 configured to supply power to one or more components of the blood pressure cuff 100. The power source 128 can include a direct current source, an alternating current source, a variable voltage source, and the like. For instance, the power source 128 can include a battery, a fuel cell, a photovoltaic cell, a piezoelectric energy device, a mechanical energy storage device, a chemical energy storage device, or other suitable energy source. The power source 128 can be coupled to the vibration sensor 102, to the mechanical cuff tensioner 106, or to the tension sensor 108, singly or in any combination. The mechanical cuff tensioner 106 can be a powered tensioner (e.g., an electrically-driven tensioner, such as an electric motor), can be a manually-tensioned tensioner, such as can be turned by hand, or a combination of manual and powered.

Figure 7:
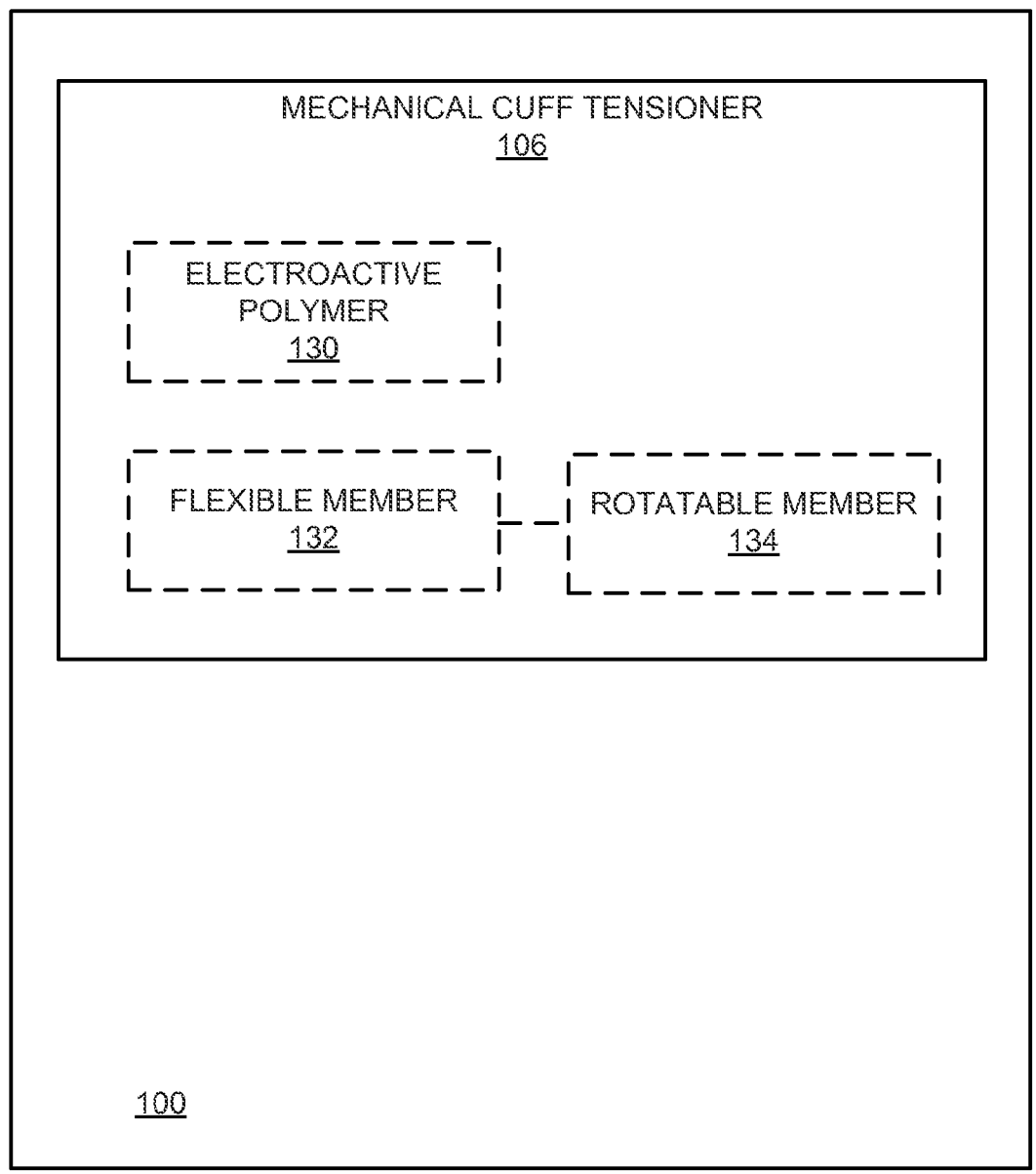
FIG. 7 is a schematic of an alternative embodiment of a blood pressure cuff.

In an embodiment, illustrated in FIG. 7, the mechanical cuff tensioner 106 includes an electroactive polymer 130. Electroactive polymers can be configured to contract upon application of a voltage. For instance, the mechanical cuff tensioner 106 can adjust a compressive force of the cuff 104 on the lumen by application of a voltage to the electroactive polymer 130 of the mechanical cuff tensioner 106. Application of the voltage to the electroactive polymer 130 can cause the electroactive polymer 130 to contract, which can cause the cuff 104 to compress the limb to increase the compressive force on the lumen. Removal of the applied voltage can cause the electroactive polymer 130 to relax (e.g., progress to a steady state position) or expand (e.g., relative to the contraction), which can reduce the compressive force of the cuff 104 on the lumen.

In an embodiment, illustrated in FIG. 7, the mechanical cuff tensioner 106 includes a flexible member 132 attached to a rotatable member 134 to adjust the compressive force of the cuff 104 on the lumen. The flexible member 132 can be configured to wind around the rotatable member 134 to tighten the cuff 104 to increase the compressive force of the cuff 104 on the lumen. The flexible member 132 can be configured to unwind around the rotatable member 134 to loosen the cuff 104 to reduce the compressive force of the cuff 104 on the lumen.

Figure 8:
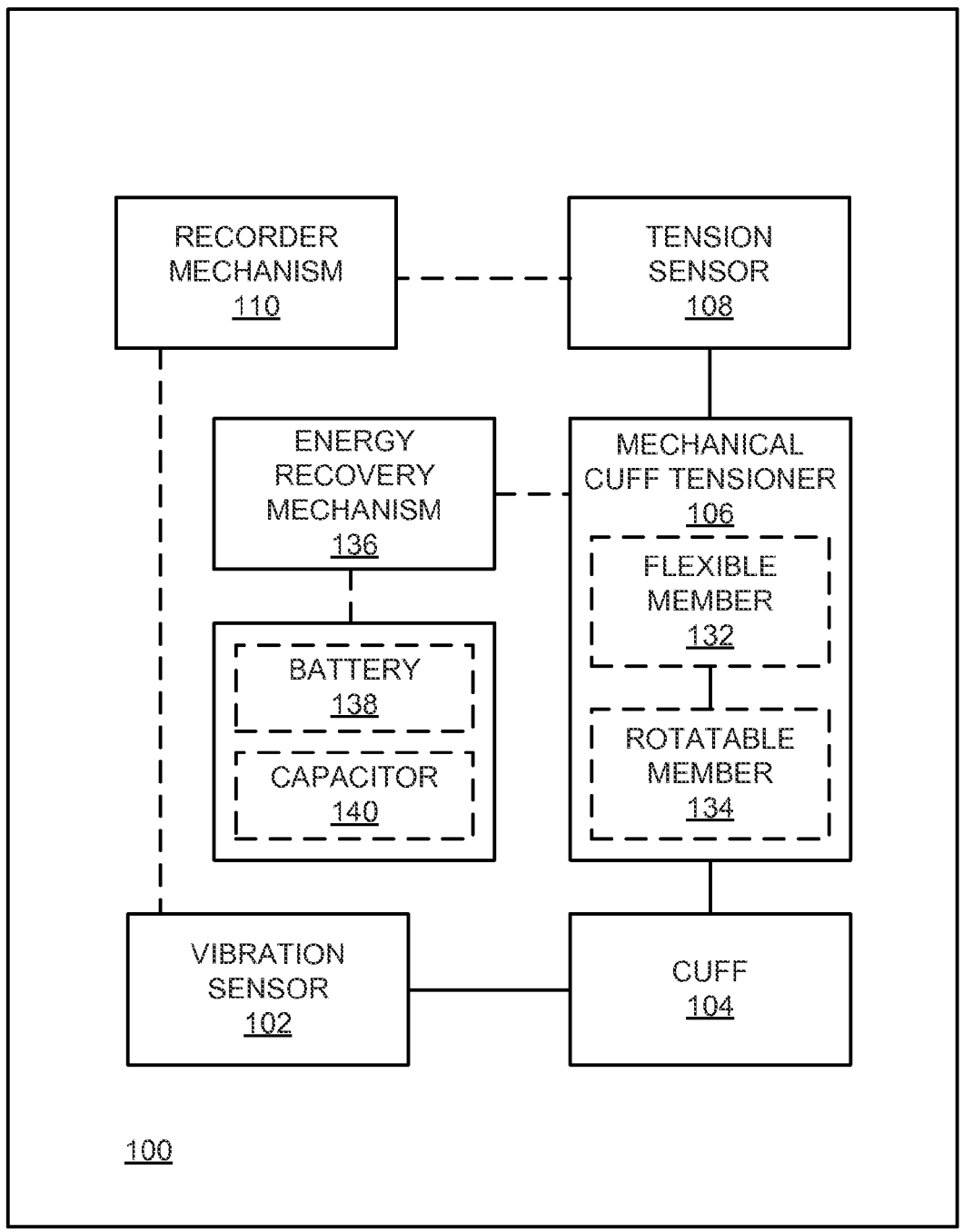
FIG. 8 is a schematic of an alternative embodiment of a blood pressure cuff.

In an embodiment, illustrated in FIG. 8, the blood pressure cuff 100 includes an energy-recovery mechanism 136 operably coupled to the mechanical cuff tensioner 106. The energy-recovery mechanism 136 can be configured to recover energy from activation of the mechanical cuff tensioner 106 to reduce the compressive force of the cuff 104 on the lumen. For instance, where the mechanical cuff tensioner 106 includes the flexible member 132 and the rotatable member 134, the energy-recovery mechanism 136 can recover energy from the unwinding of the flexible member 132 around the rotatable member 134 when the cuff 104 loosens and reduces the compressive force of the cuff 104 on the lumen. The energy-recovery mechanism 136 can include a piezoelectric generator, an electromechanical generator, a magnetic generator, a mechanical generator (e.g., a generator employing a spring, turbine, or piston), an electroactive polymer, or another suitable device for recovering energy from the activation of the mechanical cuff tensioner 106 to reduce the compressive force of the cuff 104 on the lumen. The blood pressure cuff 100 can include a battery 138 coupled to the energy-recovery mechanism 136 and configured to store the recovered energy from the energy-recovery mechanism 136. The blood pressure cuff 100 can include a capacitor 140 coupled to the energy-recovery mechanism 136 and configured to buffer the recovered energy from the energy-recovery mechanism 136. The mechanical cuff tensioner 106 can be mechanically powered, battery powered, or powered through other suitable means.

Figure 9:
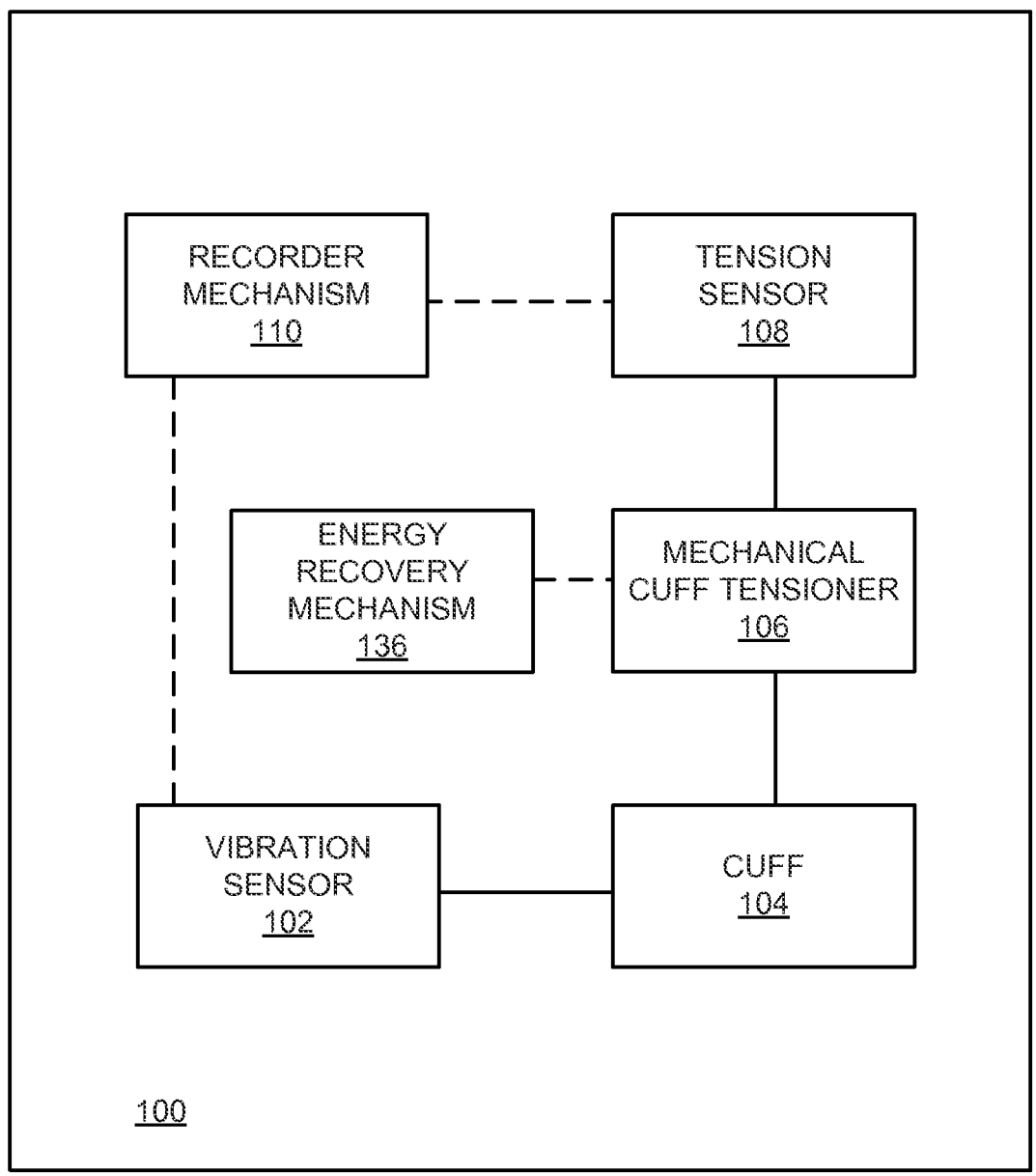
FIG. 9 is a schematic of an alternative embodiment of a blood pressure cuff.
Figure 10:
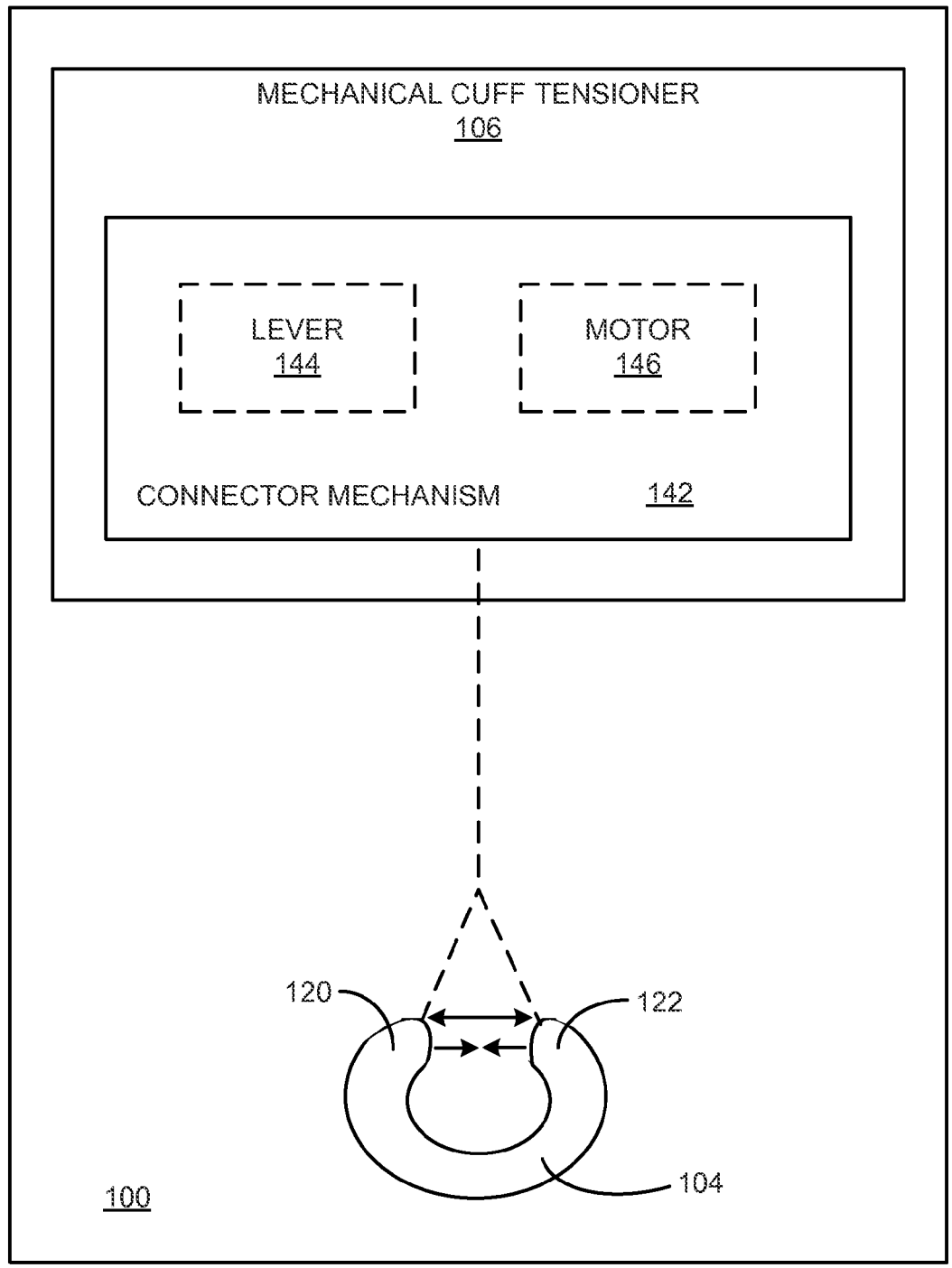
FIG. 10 is a schematic of an alternative embodiment of a blood pressure cuff.

In an embodiment, illustrated in FIGS. 9 and 10, the blood pressure cuff 100 includes the energy-recovery mechanism 136 operably coupled to the mechanical cuff tensioner 106. The energy-recovery mechanism 136 can be configured to recover energy from activation of the mechanical cuff tensioner 106 to reduce the compressive force of the cuff 104 on the lumen. In an embodiment, the energy-recovery mechanism 136 can be configured to recover energy from activation of the mechanical cuff tensioner 106 to reduce the compressive force of the cuff 104 on the lumen when the mechanical cuff tensioner 106 was tensioned or tightened manually, such as by hand. The mechanical cuff tensioner 106 can include a connector mechanism 142 configured to position a first end 120 the cuff 104 in proximity to a second end 122 of the cuff 104. The connector mechanism 142 can be configured to adjust the compressive force of the cuff 104 on the lumen by adjusting the position of the first end 120 of the cuff 104 relative to the position of the second end 122 of the cuff 104. For instance, by bringing the first end 120 of the cuff 104 closer to the second end 122 of the cuff 104, the compressive force of the cuff 104 on the lumen can be increased. In an embodiment, the connector mechanism 142 includes a lever 144 for positioning one or more of the first end 120 and the second end 122. For instance, the lever 144 can provide a force multiplier which can apply more force to pull the ends (120, 122) together (if non-overlapping) or cinches the mechanical cuff tensioner 106 (increasing an existing overlap). The lever 144 can include a screw, a scissors mechanism, or other suitable device. In an embodiment, the connector mechanism 142 includes a motor 146 for positioning one or more of the first end 120 and the second end 122.

Figure 11:
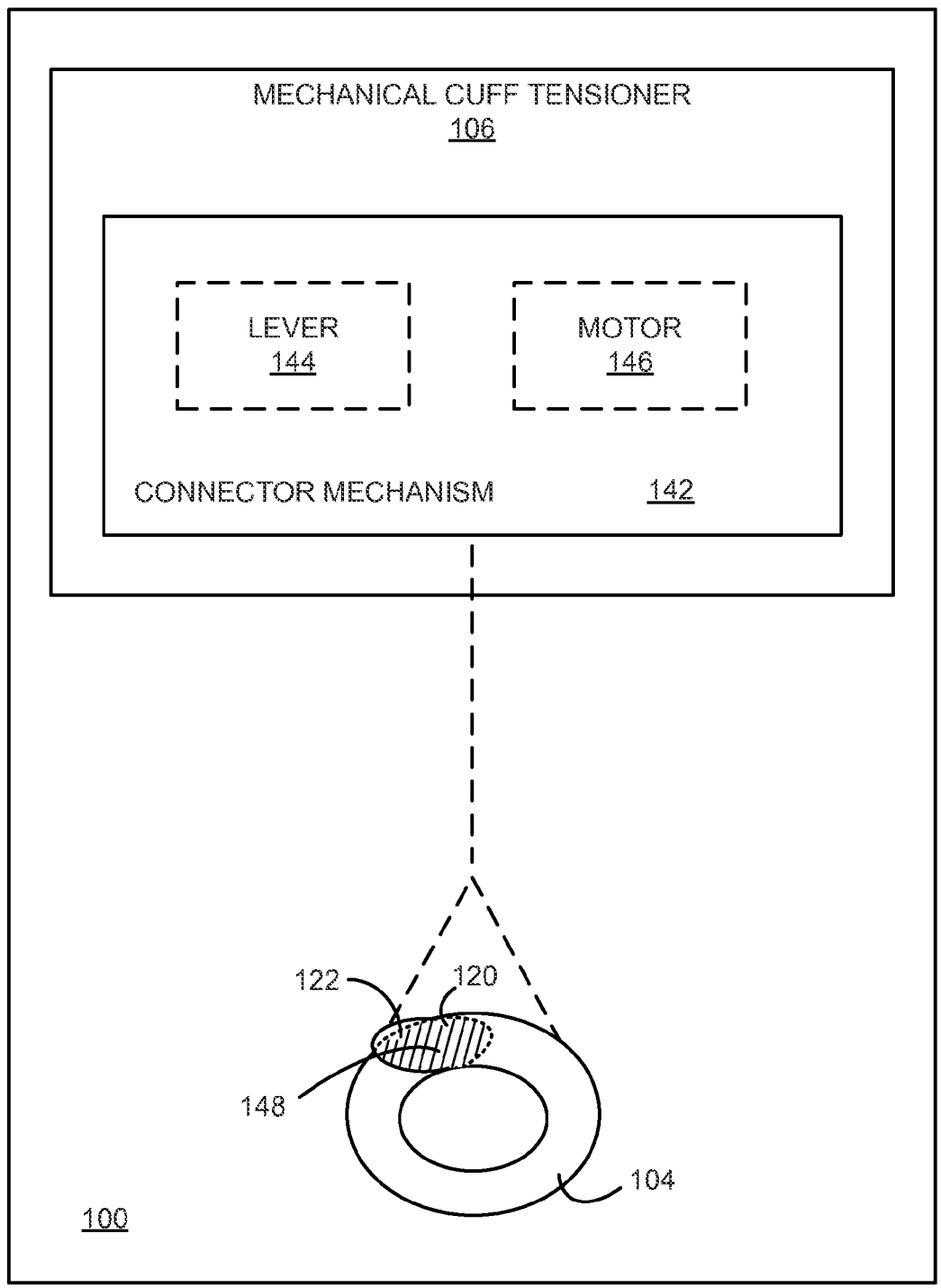
FIG. 11 is a schematic of an alternative embodiment of a blood pressure cuff.

In an embodiment, illustrated in FIG. 11, the mechanical cuff tensioner 106 includes the connector mechanism 142, where the connector mechanism 142 is configured to overlap at least a portion of the cuff 104. The connector mechanism 142 can be configured to adjust the compressive force of the cuff 104 on the lumen by adjusting the overlap. For instance, the connector mechanism 142 can be configured to overlap at least a portion of the first end 120 and the second end 122 of the cuff 104 to form overlap portion 148. By increasing the area of the overlap portion 148, the compressive force of the cuff 104 on the lumen can be increased. By decreasing the area of the overlap portion 148, the compressive force of the cuff 104 on the lumen can be decreased. In an embodiment, the connector mechanism 142 includes a lever 144 for positioning the first end 120 relative to the second end 122 to control the overlap portion 148. In an embodiment, the connector mechanism 142 includes a motor 146 for positioning the first end 120 relative to the second end 122 to control the overlap portion 148.

The tension sensor 108 can be configured to halt adjustment of the compressive force of the cuff 104 on the lumen by the mechanical cuff tensioner 106 at a designated pressure. For instance, the designated pressure can be a pressure suitable for the vibration sensor 102 to sense blood flow in the lumen. Where the pressure is not suitable for the vibration sensor 102 to sense blood flow in the lumen, the tension sensor 108 can permit the mechanical cuff tensioner 106 to adjust the compressive force of the cuff 104 on the lumen until the designated pressure is attained.

Figure 12:
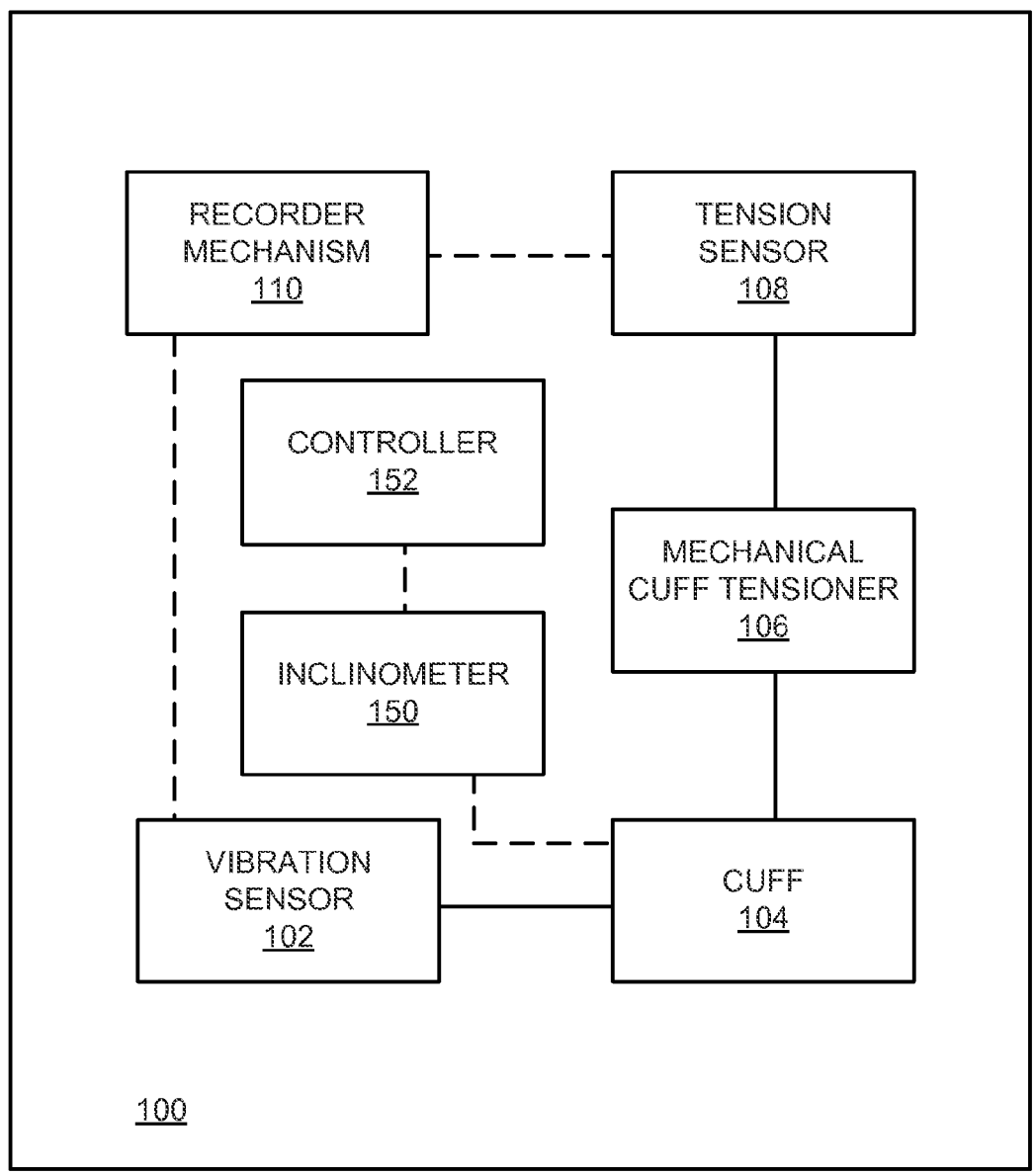
FIG. 12 is a schematic of an alternative embodiment of a blood pressure cuff.

In an embodiment, as illustrated in FIG. 12, the blood pressure cuff 100 includes an inclinometer 150 operably coupled to the cuff 104. The inclinometer 150 can be configured to detect an orientation of the cuff 104. In an embodiment, the motion sensor 118 and the inclinometer 150, either singularly or together can provide information that indicates that the cuff 104 has been oriented to a substantially horizontal position indicating that it is not an optimal time to measure blood pressure, for example if the user is engaging in an athletic activity, or when the cuffed limb may be elevated higher than the heart. The orientation of the cuff 104 can affect the determination of a blood pressure in the lumen by the blood pressure cuff 100. The vibration sensor 102 can be configured to activate when the orientation is detected to be within a specified range. For instance, the specified range can be determined to be a range within which the determination of the blood pressure in the lumen can be made with relatively accurate results (e.g., within a particular standard deviation). The blood pressure cuff 104 can also include a controller 152 configured to determine a correction factor based upon the orientation. The controller 152 can include a processor, microprocessor, or other device suitable for performing calculations. The controller 152 may include or may be operably coupled to a memory for storing one or more values used for calculations. The correction factor can be utilized to increase the accuracy of the determination of the blood pressure in the lumen by the blood pressure cuff 100. As an example, the correction factor can be determined by measuring an angle-from-vertical with the inclinometer 150, where the limb hangs from a pivot point (such as a shoulder where the limb is an arm). The cosine of the angle indicates the vertical offset from the pivot point. For an individual with an upright torso (e.g., when sitting or standing), the cosine of the angle provides the vertical offset of the cuff 104 an compared to the heart (e.g., where the heart-to-shoulder distance is treated as fixed). The vertical offset can provide a pressure-head correction factor accordingly.

Figure 13:
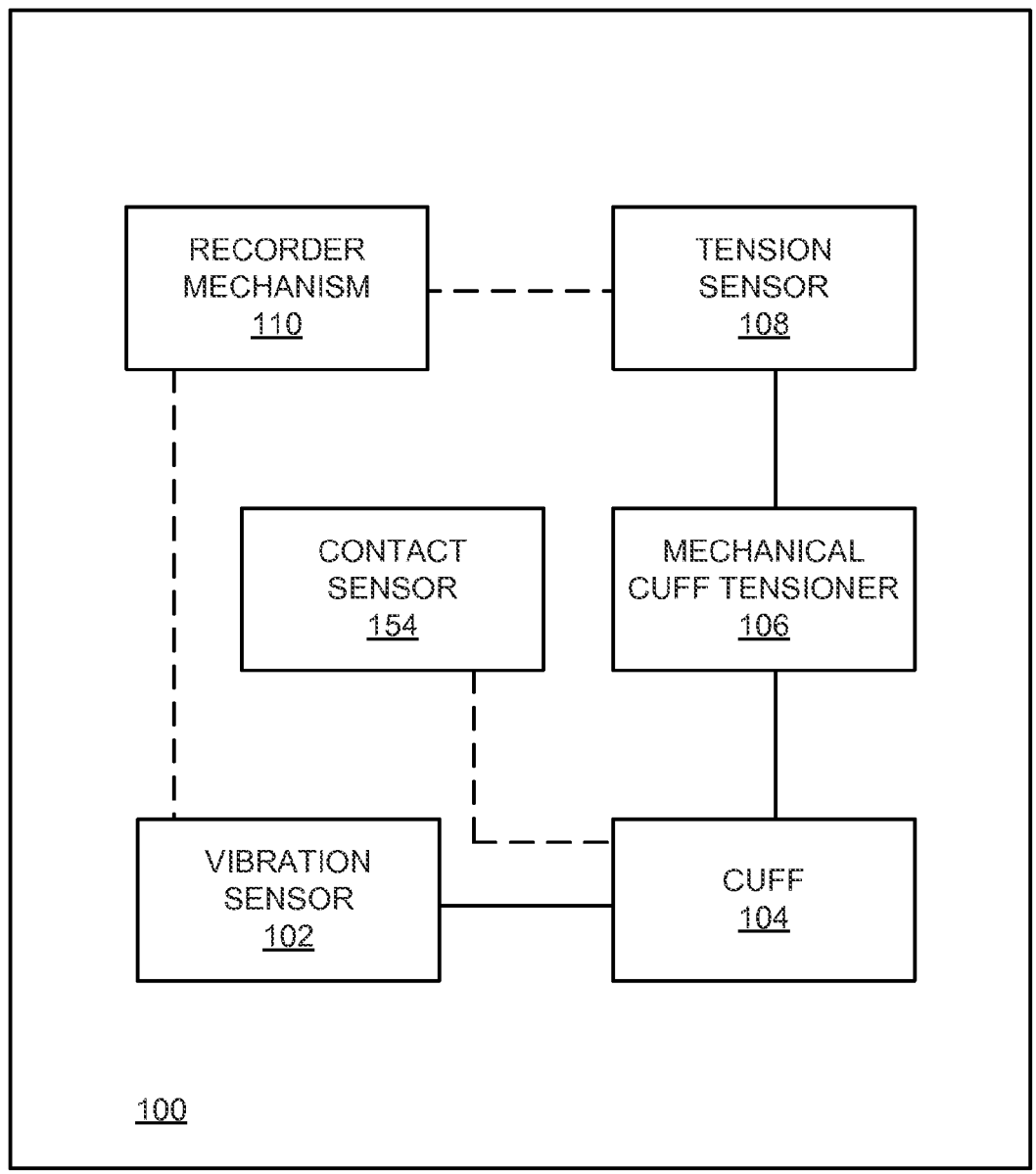
FIG. 13 is a schematic of an alternative embodiment of a blood pressure cuff.

In an embodiment, as illustrated in FIG. 13, the blood pressure cuff 100 includes a contact sensor 154 operably coupled to the cuff 104. The contact sensor can be configured to determine contact between the limb and a torso of the human or animal. The vibration sensor 102 can be configured to activate when contact is determined to occur between the limb and the torso. For example, when contact is determined, the contact sensor 154 can generate a control signal which can be transmitted to the vibration sensor 102. The control signal can direct the vibration sensor 102 to activate. When no contact occurs, the conditions for determining blood pressure in the lumen may not be ideal, as the limb can be oriented in a manner that would affect blood pressure determinations.

Figure 14:
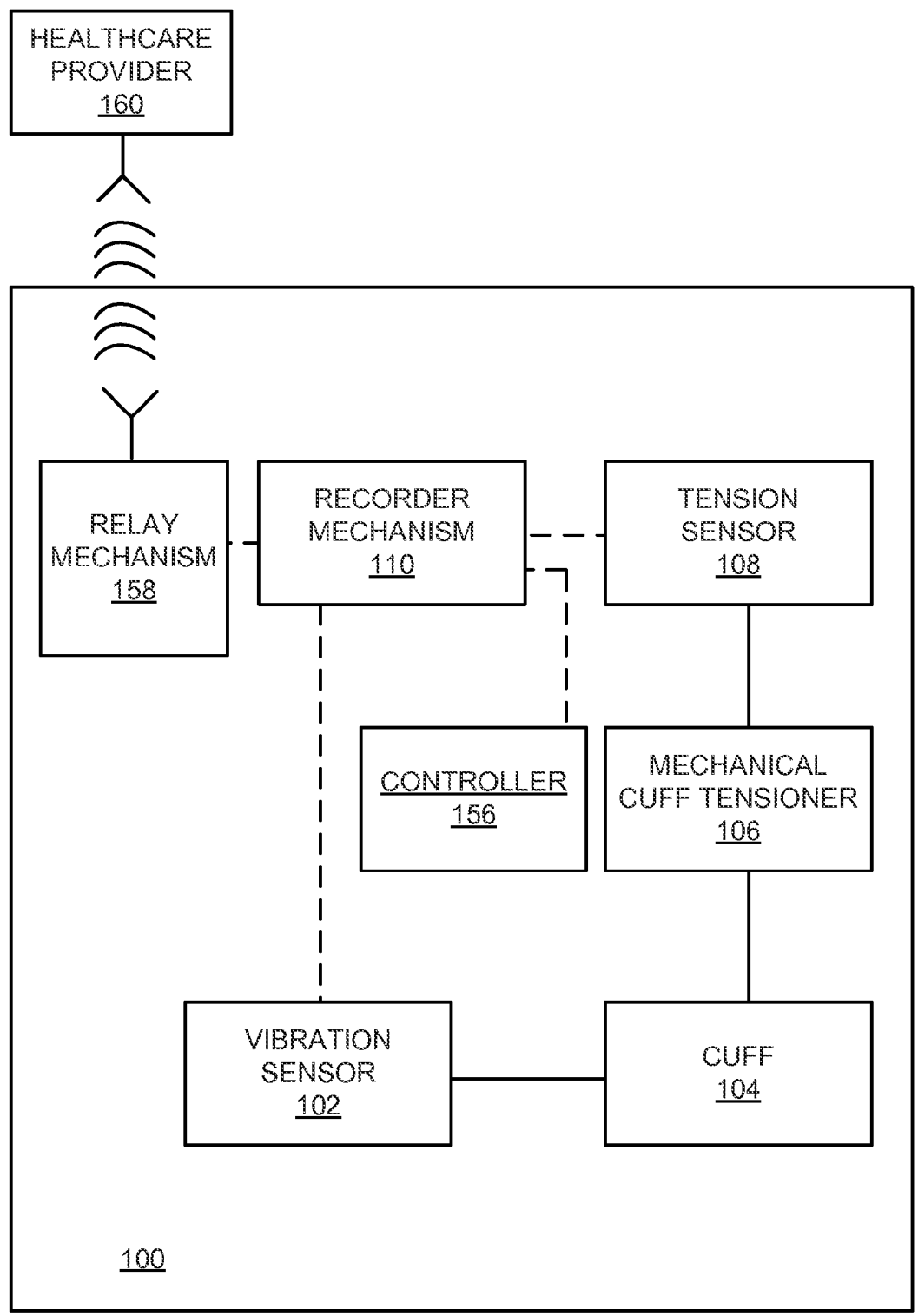
FIG. 14 is a schematic of an alternative embodiment of a blood pressure cuff.
Figure 15:
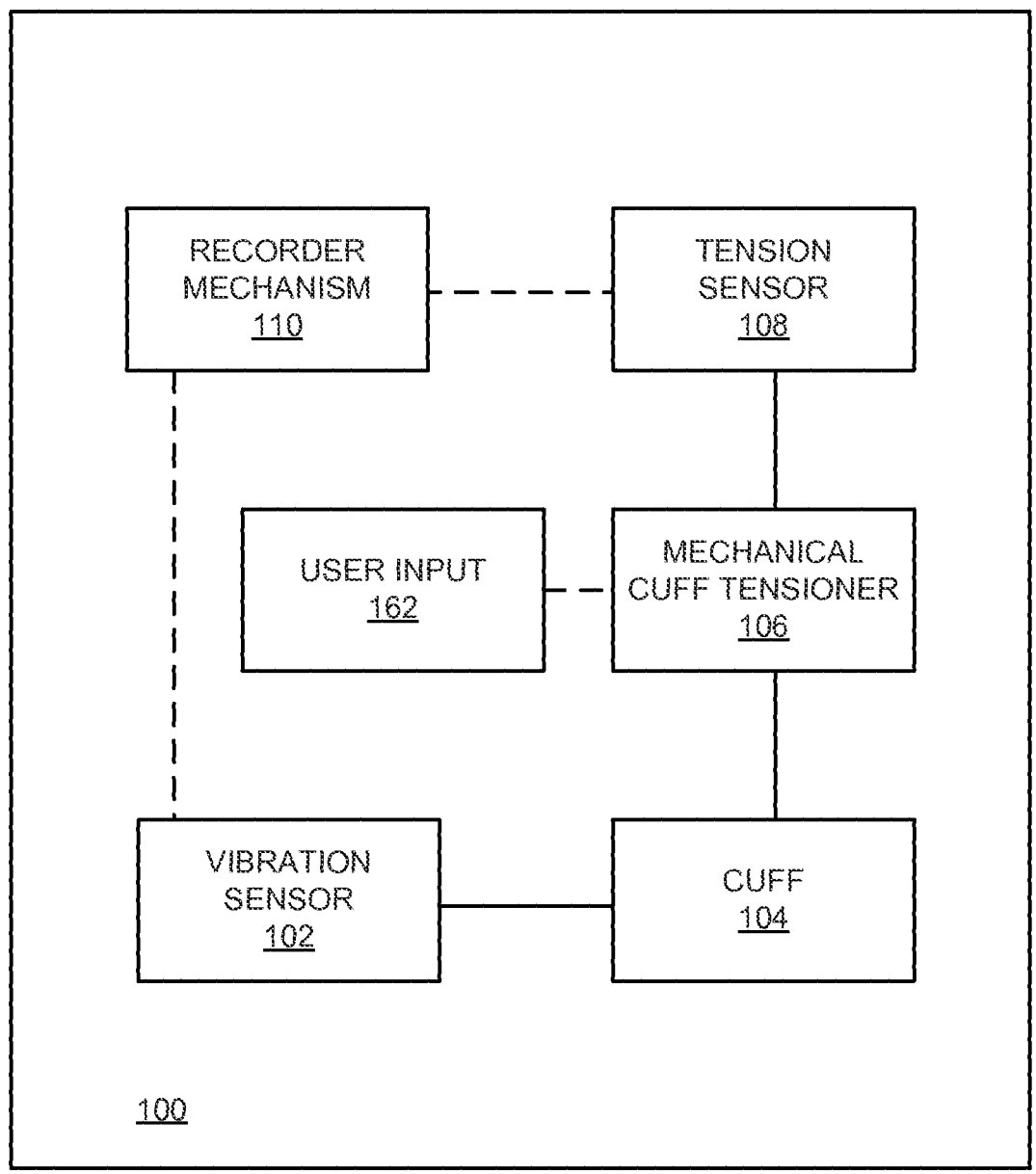
FIG. 15 is a schematic of an alternative embodiment of a blood pressure cuff.

In an embodiment, as illustrated in FIG. 14, the blood pressure cuff 100 includes a controller 156 operably coupled to the recorder mechanism 110. The controller 156 can be configured to determine a blood pressure value based on the first tension value from the tension sensor 108, the second tension value from the tension sensor 108, the first measurement by the vibration sensor 102, and the second measurement by the vibration sensor 102. For example, the blood pressure value determined by the controller 156 can include a systolic blood pressure and a diastolic blood pressure. The tension values provided by the tension sensor 108 can be utilized to determine pressure values associated with the measurements made by the vibration sensor 102. The controller 156 can be configured to determine the pressure values and to correlate the pressure values with the measurements made by the vibration sensor 102 in order to determine the blood pressure value. The recorder mechanism 110 can be configured to record the determined blood pressure value from the controller 156. The blood pressure cuff 100 can also include a relay mechanism 158 operably coupled to the recorder mechanism 158. The relay mechanism 158 can be configured to relay the determined blood pressure value recorded by the recorder mechanism 110 to a healthcare provider 160. The relay mechanism 158 can include a transmitter, a transceiver, wireless communication system, wired communication system, or the like. The relay mechanism 158 can be configured to immediately relay to the healthcare provider 160 the determined blood pressure value when the determined blood pressure value is at least one of above a threshold value, below the threshold value, or irregular. The relay mechanism 158 can be configured to relay to the healthcare provider 160, according to a schedule, the determined blood pressure value when the determined blood pressure value is within a normal range. The controller 156 can be configured to identify the determined blood pressure value as being at least one of above a threshold value, below the threshold value, or at the threshold value. For example, the threshold value can be stored in a memory, where the memory is operably coupled to the controller 156 such that the controller 156 can compare the determined blood pressure value to the threshold value. The threshold value also can be wirelessly accessed by the blood pressure cuff 100, such as via the cloud (e.g., an individual's settings stored in a medical record). The controller 156 can be configured to generate an alert based upon the determined blood pressure value. For instance, where the determined blood pressure value is identified as being above a threshold value or below the threshold value, the controller 156 can generate an alert, which can be relayed to the healthcare provider 160 via the relay mechanism 158. The alert generated by the controller 156 can be provided locally to a user of the blood pressure cuff 100, such as through a speaker or other auditory device (not shown).

The vibration sensor 102 can be configured to measure a pulse rate of blood in the lumen. For example, the pulse rate can be measured as the number of pulses in a unit time, such as the number of pulses per minute, i.e., the inverse of the time between pulses (e.g., between the peaks of consecutive pulses). The recorder mechanism 110 can be configured to record the measured pulse rate. The relay mechanism 158 can be configured to relay the measured pulse rate to the healthcare provider 160. The relay mechanism 158 can be configured to immediately relay to the healthcare provider 160 the measured pulse rate when the measured pulse rate is at least one of above a threshold value, below the threshold value, or irregular. The relay mechanism 158 can be configured to relay to the healthcare provider 160, according to a schedule, the measured pulse rate when the measured pulse rate is within a normal range. The controller 156 can be configured to identify the measured pulse rate as being at least one of above a threshold value, below the threshold value, or at the threshold value. For example, the threshold value can be stored in a memory, where the memory is operably coupled to the controller 156 such that the controller 156 can compare the measured pulse rate to the threshold value. The controller 156 can be configured to generate an alert based upon the measured pulse rate. For instance, where the measured pulse rate is identified as being above a threshold value or below the threshold value, the controller 156 can generate an alert, which can be relayed to the healthcare provider 160 via the relay mechanism 158. The alert generated by the controller 156 can be provided locally to a user of the blood pressure cuff 100, such as through a speaker or other auditory device (not shown).

The vibration sensor 102 can be configured to measure a pulse structure of blood in the lumen. For example, the pulse structure can include the pressure profile of a single pulse of blood, such as the fine-grained data associated with a pulse. The recorder mechanism 110 can be configured to record the measured pulse structure. The relay mechanism 158 can be configured to relay the measured pulse structure to the healthcare provider 160. The relay mechanism 158 can be configured to immediately relay to the healthcare provider 160 the measured pulse structure when the measured pulse structure is at least one of above a threshold value, below the threshold value, or irregular. For example, the threshold value can be stored in a memory, where the memory is operably coupled to the controller 156 such that the controller 156 can compare the measured pulse structure to the threshold value. The relay mechanism 158 can be configured to relay to the healthcare provider 160, according to a schedule, the measured pulse structure when the measured pulse structure is within a normal range. The controller 156 can be configured to identify the measured pulse structure as being at least one of above a threshold value, below the threshold value, or at the threshold value. The controller 156 can be configured to generate an alert based upon the measured pulse structure. For instance, where the measured pulse structure is identified as being above a threshold value or below the threshold value, the controller 156 can generate an alert, which can be relayed to the healthcare provider 160 via the relay mechanism 158. The alert generated by the controller 156 can be provided locally to a user of the blood pressure cuff 100, such as through a speaker or other auditory device (not shown).

The mechanical cuff tensioner 106 can be configured to activate or deactivate according to one or more of a plurality of methods. For instance, the mechanical cuff tensioner 106 can be configured to adjust the compressive force of the cuff 104 on the lumen according to a scheduled activation. In an embodiment, illustrated in FIG. 15, the blood pressure cuff 100 includes a user input device 162. The mechanical cuff tensioner 106 can be configured to adjust the compressive force of the cuff 104 on the lumen upon a user-given command via the user input device 162. The user-given command can indicate immediate activation, or can be delayed activation, such as through specification of a certain activation time, activation delay, activation schedule, or the like, which can be stored in a memory via the recorder mechanism 110. For instance, the mechanical cuff tensioner 106 can be configured to automatically reduce compressive force applied to the lumen by the cuff 104 upon occurrence of an event, where the event can include a user-given command via the user input device 162. The user input device can include one or more of a keypad, a touchscreen, a voice recognition module, and a remote input device which communicates wirelessly with the cuff 104 (e.g., a cell phone application or computer program used to modify cuff settings).

Figure 16:
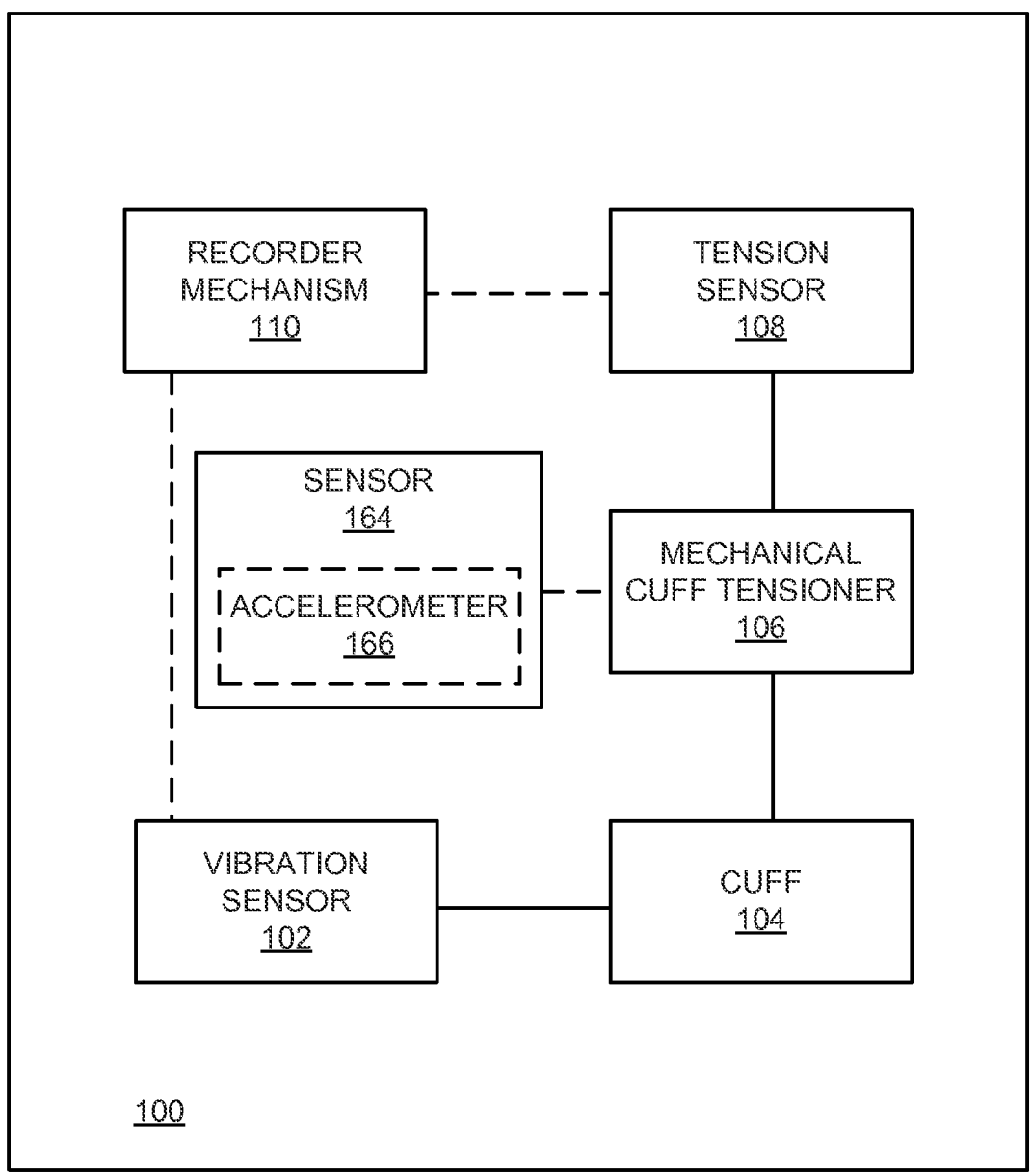
FIG. 16 is a schematic of an alternative embodiment of a blood pressure cuff.

In an embodiment, illustrated in FIG. 16, the blood pressure cuff 100 includes a sensor 164 configured to sense a physiological condition of the human or animal. The sensor 164 can be a blood oxygenation sensor, a pulse sensor, a moisture sensor (e.g., for perspiration determination), a temperature sensor (e.g., for skin temperature determination), a pH sensor, an EKG or micro-impulse radar (e.g., for heart activity determination) or other suitable sensor. The mechanical cuff tensioner 196 can be configured to adjust the compressive force of the cuff 104 on the lumen upon the sensed physiological condition. The sensed physiological condition can be one or more of a blood oxygenation level and a pulse rate. The sensor 164 can be configured to sense a user activity level, where the mechanical cuff tensioner 106 is configured to adjust the compressive force of the cuff 104 on the lumen upon the user activity level. The user activity level can be one or more of a systemic activity level and a local activity level. Systemic activity can include a measurement of an activity over a period of time, such as an average activity over a day, a number of steps per day, a number of times getting out of a chair per day, a total elevation change over a day, and the like. Local activity can include current activity (e.g., instantaneous or within the least few minutes), such as speed of movement, determining elevation change through standing from a chair or climbing stairs, and the like. The user activity level can include motion of the limb. In an embodiment, the motion of the limb can be measured by the sensor 164 including an accelerometer 166.

Figure 17:
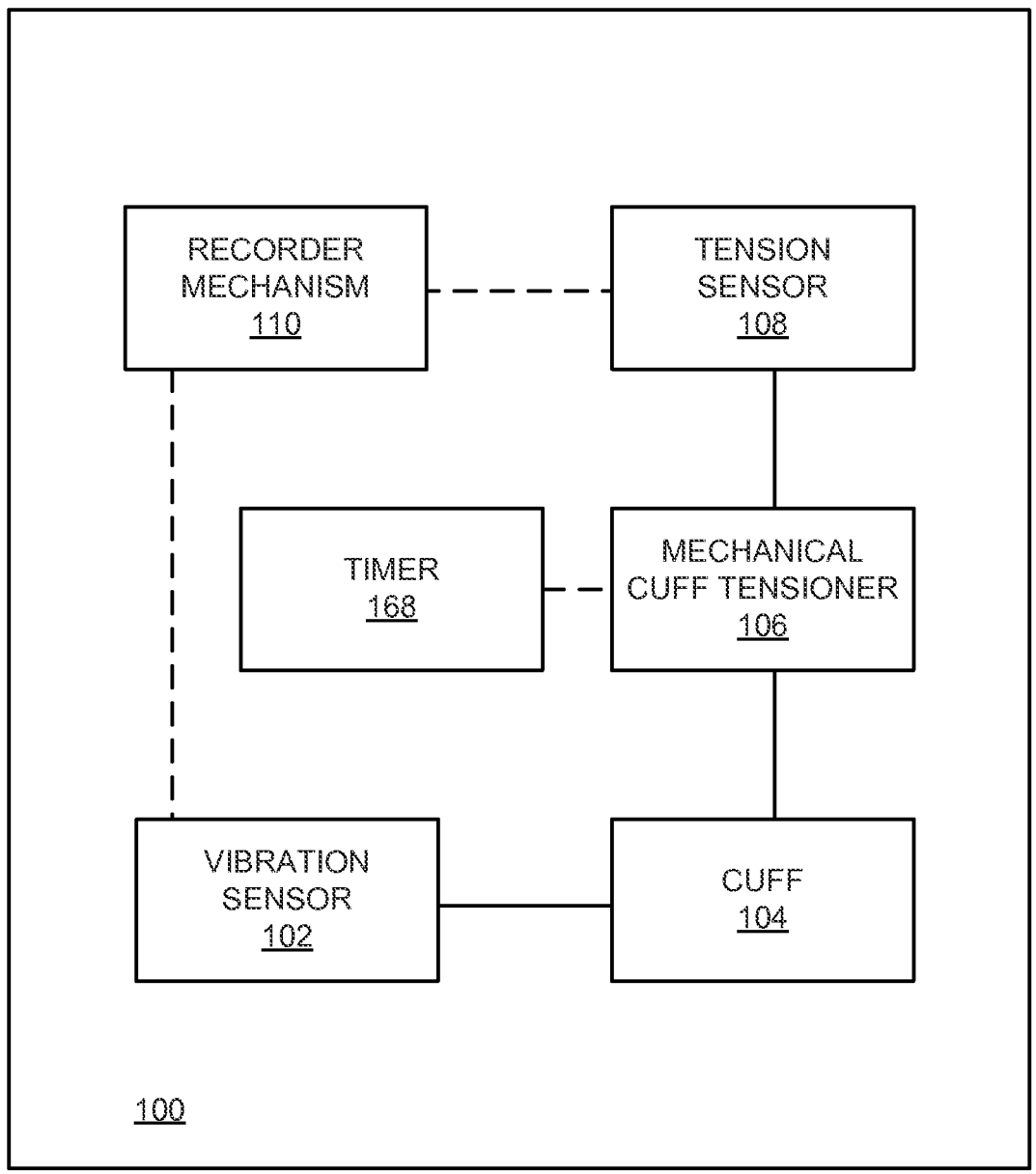
FIG. 17 is a schematic of an alternative embodiment of a blood pressure cuff.

In an embodiment, illustrated in FIG. 17, the blood pressure cuff 100 includes a timer device 168 operably coupled to the mechanical cuff tensioner 106. The timer device 168 can be configured to measure a time-at-tension value of the mechanical cuff tensioner 106. The mechanical cuff tensioner 106 can be configured to automatically reduce compressive force applied to the lumen upon occurrence of an event, wherein the event is exceeding a specified time-at-tension value measured by the timer device 168. In an embodiment, the time-at-tension value is a non-transient value. The timer device 168 can provide tension values to the timer device 168 (or associated controller). When the tension values are substantially constant (e.g., within a range or standard deviation), then the timer device 168 or associated controller determines a steady tension value, rather than a transitory tension value.

The mechanical cuff tensioner 106 can be configured to automatically reduce compressive force applied to the lumen upon occurrence of an event, where the event is a tension value measured by the tension sensor 108 reaching a maximum tension limit. The maximum tension limit can be one or more of a preset limit and a user-specified limit. A controller can compare a current tension value measured by the tension sensor 108 with a maximum tension limit value that can be stored in memory. Such comparison can be periodic or constant.

Referring now to FIGS. 18-29, a blood pressure cuff 200 is described in accordance with the present disclosure. The blood pressure cuff 200 can generally include a vibration sensor 202, a cuff 204, a cuff pressurizer 206, and an energy-generating apparatus 208. The blood pressure cuff 200 can be configured to contact a limb of human or animal and to measure or derive a blood pressure of blood within a lumen of the human or animal. The limb can include an arm, a leg, a finger, or a toe of the human or animal.

Figure 18:
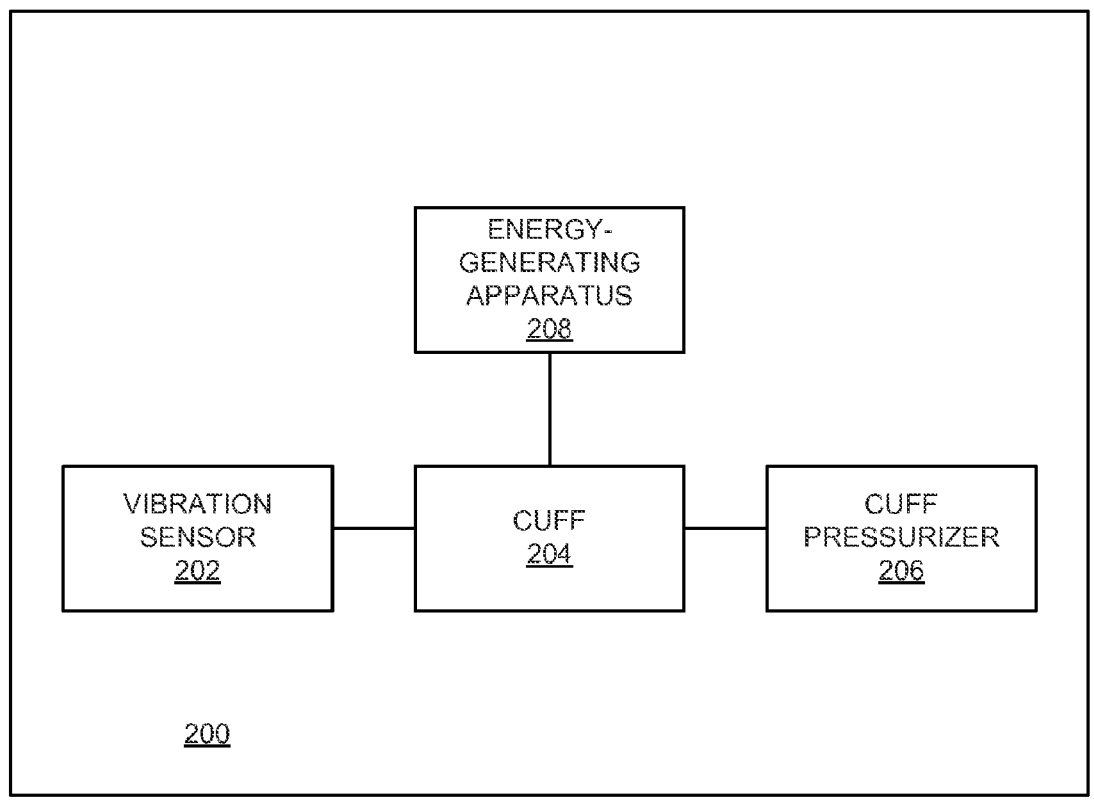
FIG. 18 is a schematic of a blood pressure cuff with an energy-recovery apparatus.

In an embodiment, illustrated in FIG. 18, the blood pressure cuff 200 includes a vibration sensor 202 configured to sense blood flow in the lumen of the human or animal, such as through proximity of the vibration sensor 202 relative to the lumen. The vibration sensor 202 can be an acoustic sensor, a piezoelectric sensor, or another suitable sensor sufficient to sense vibrations of blood flow in the lumen of the human or animal. The blood pressure cuff 200 also includes a cuff 204 coupled to the vibration sensor 202 and configured to contact the limb of the human or animal. The cuff 204 can be configured for contacting the limb of the human or animal to secure the blood pressure cuff 200 in place for a duration sufficient for the vibration sensor 202 to sense the blood flow in the lumen. The blood pressure cuff 200 also includes a cuff pressurizer 206 coupled to the cuff 204. The cuff pressurizer 206 is configured to adjust a compressive force of the cuff 204 on the lumen. For instance, the cuff pressurizer 206 is configured to tension and de-tension the cuff 204 about the limb. The cuff pressurizer 206 and the cuff 204 can act in conjunction to secure the blood pressure cuff 200 in place for a duration sufficient for the vibration sensor 202 to sense the blood flow in the lumen, which can include a plurality of sensed blood flow characteristics. The blood pressure cuff 200 also includes an energy-generating apparatus 208 coupled to the cuff 204. The energy-generating apparatus 208 can be configured to generate energy from a depressurization of the cuff 204.

Figure 19:
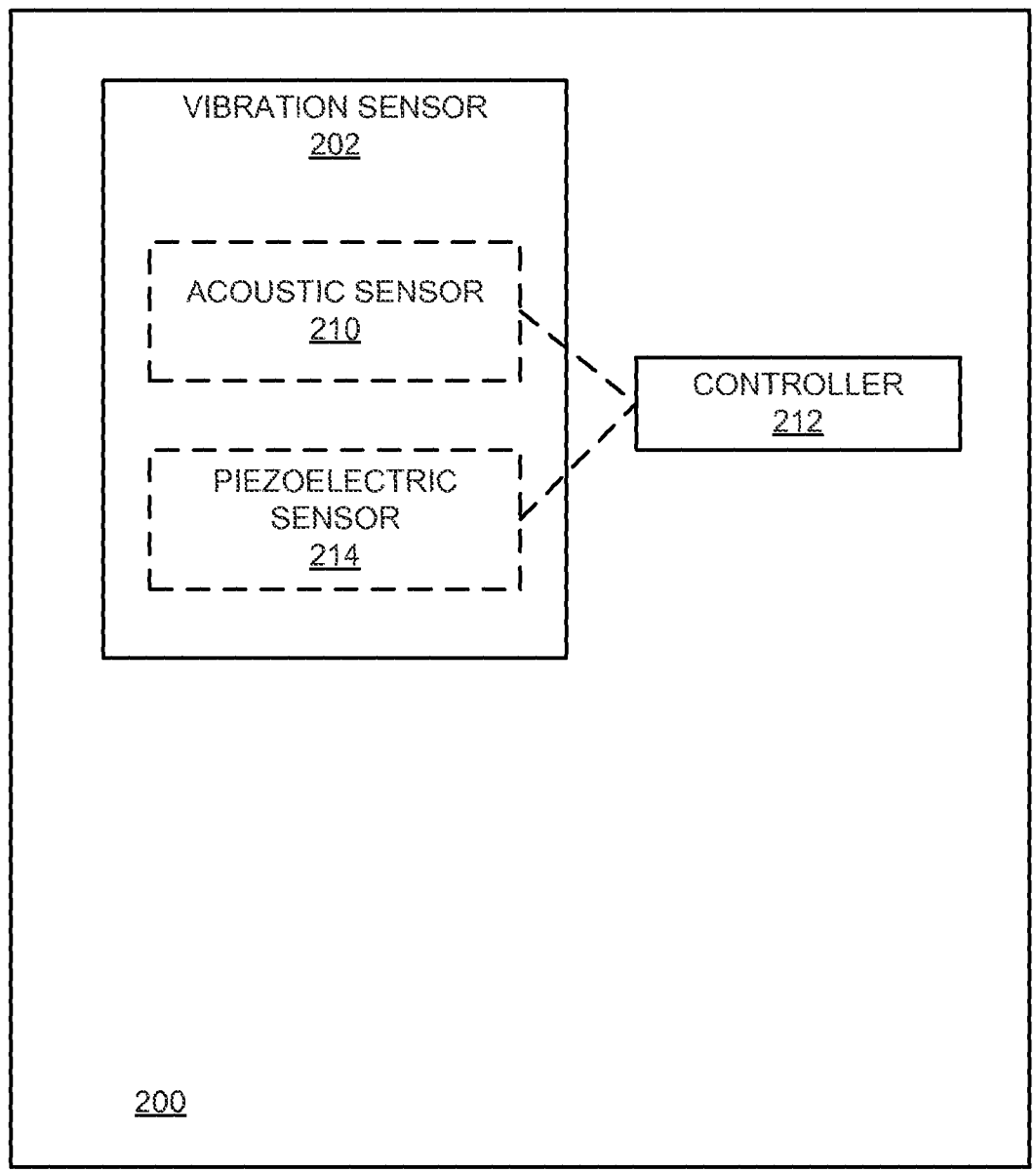
FIG. 19 is a schematic of an alternative embodiment of a blood pressure cuff.

In an embodiment, illustrated in FIG. 19, the vibration sensor 202 of the blood pressure cuff 200 can include an acoustic sensor 210. The blood pressure cuff 100 can also include a controller 212 operably coupled to the acoustic sensor 210. The controller 212 can include circuitry to determine a Korotkoff sound indicative of at least one systole and diastole. The determination of the Korotkoff sound can be based on one or more measurements made by the acoustic sensor 210. The vibration sensor 202 can also or alternatively include a piezoelectric sensor 214. The controller 212 can be operably coupled to the piezoelectric sensor 214 can include circuitry to determine at least one vibration pattern indicative of systole and diastole. The determination of the at least one vibration pattern can be based on one or more measurements made by the piezoelectric sensor 214. Such determinations of a Korotkoff sound indicative of at least one systole and diastole and of at least one vibration pattern indicative of systole and diastole can be utilized to correlate the systolic blood pressure and the diastolic blood pressure of the blood flow through the lumen of the human or animal.

Figure 20:
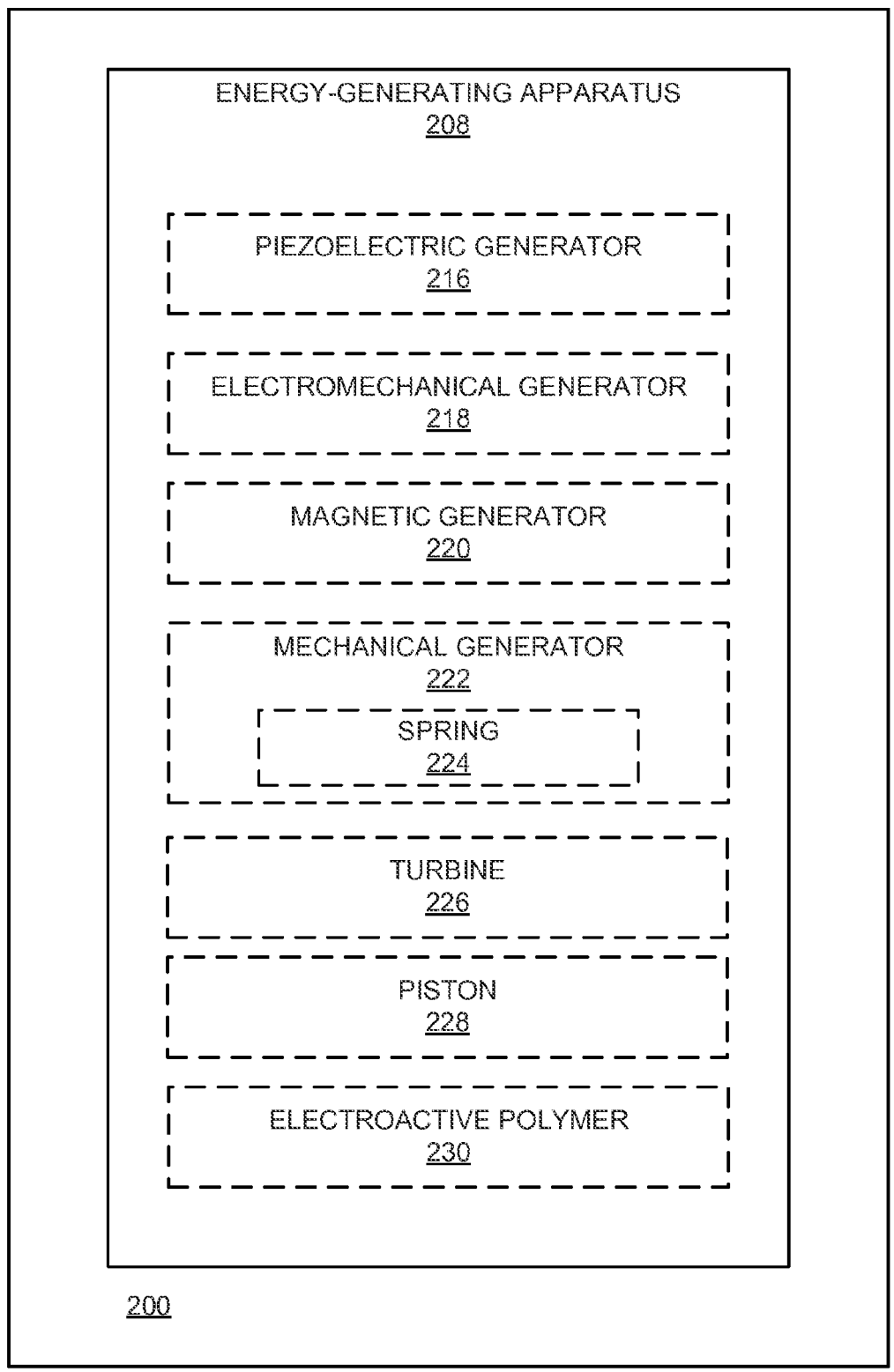
FIG. 20 is a schematic of an alternative embodiment of a blood pressure cuff.

In an embodiment, illustrated in FIG. 20, the energy-generating apparatus 208 includes one or more mechanisms to generate energy from depressurization of the cuff 204. For instance, the energy-generating apparatus 208 can include one or more of a piezoelectric generator 216, an electromechanical generator 218, a magnetic generator 220, a mechanical generator 222 (e.g., a mechanical generator employing a spring 224 to mechanically store energy from the depressurization by coiling of the spring 224), a turbine 226, a piston 228, and an electroactive polymer 230.

Figure 21:
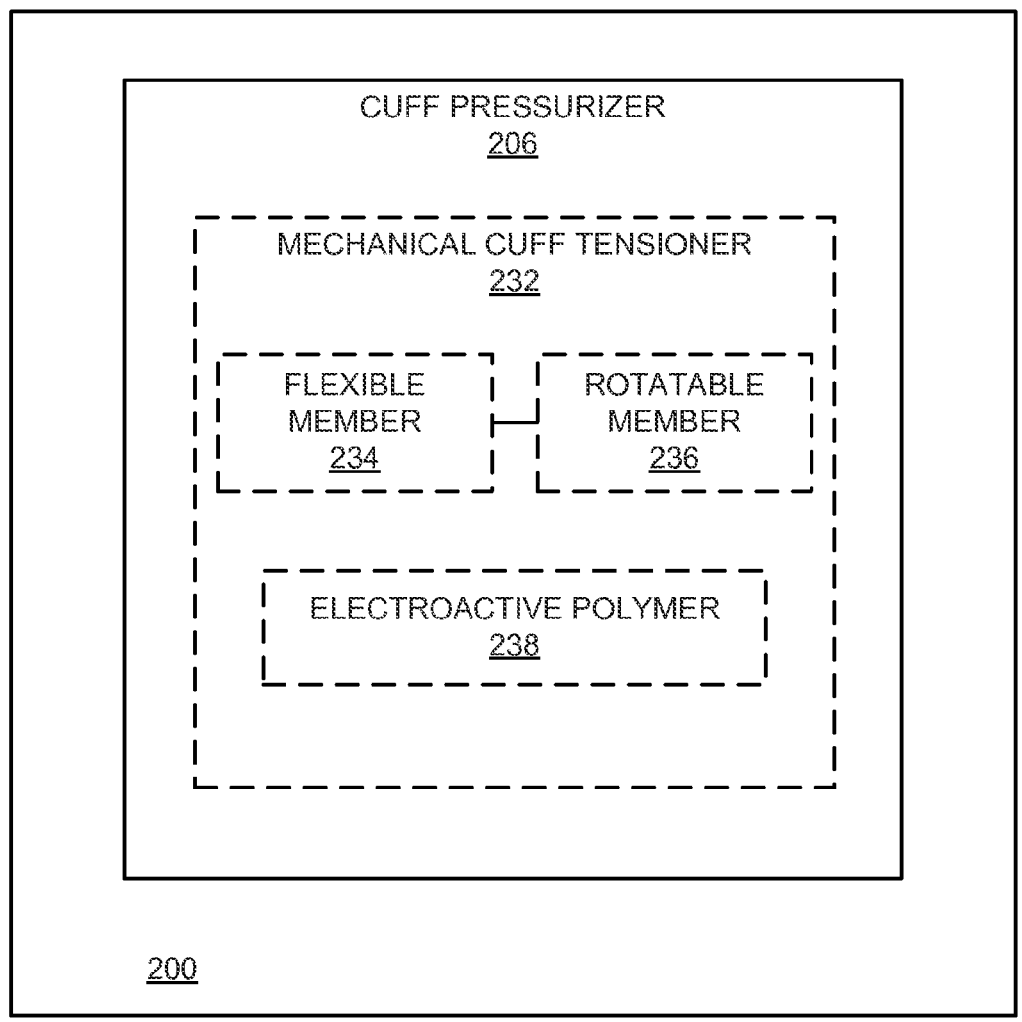
FIG. 21 is a schematic of an alternative embodiment of a blood pressure cuff.

In an embodiment, illustrated in FIG. 21, the cuff pressurizer 206 includes a mechanical cuff tensioner 232. The mechanical cuff tensioner 232 can include a flexible member 234 attached to a rotatable member 236 to adjust the compressive force of the cuff 204 on the lumen. The flexible member 234 can be configured to wind around the rotatable member 236 to tighten the cuff 204 to increase the compressive force of the cuff 204 on the lumen. The flexible member 234 can be configured to unwind around the rotatable member 236 to loosen the cuff 204 to reduce the compressive force of the cuff 204 on the lumen. The mechanical cuff tensioner 232 can additionally or alternatively include an electroactive polymer 238. Electroactive polymers can be configured to contract upon application of a voltage. For instance, the mechanical cuff tensioner 232 can adjust a compressive force of the cuff 204 on the lumen by application of a voltage to the electroactive polymer 238 of the mechanical cuff tensioner 232. Application of the voltage to the electroactive polymer 238 can cause the electroactive polymer 238 to contract, which can cause the cuff 204 to compress the limb. Removal of the applied voltage can cause the electroactive polymer 238 to relax (e.g., progress to a steady state position) or expand (e.g., relative to the contraction), which can reduce the compressive force of the cuff 204 on the lumen.

Figure 22:
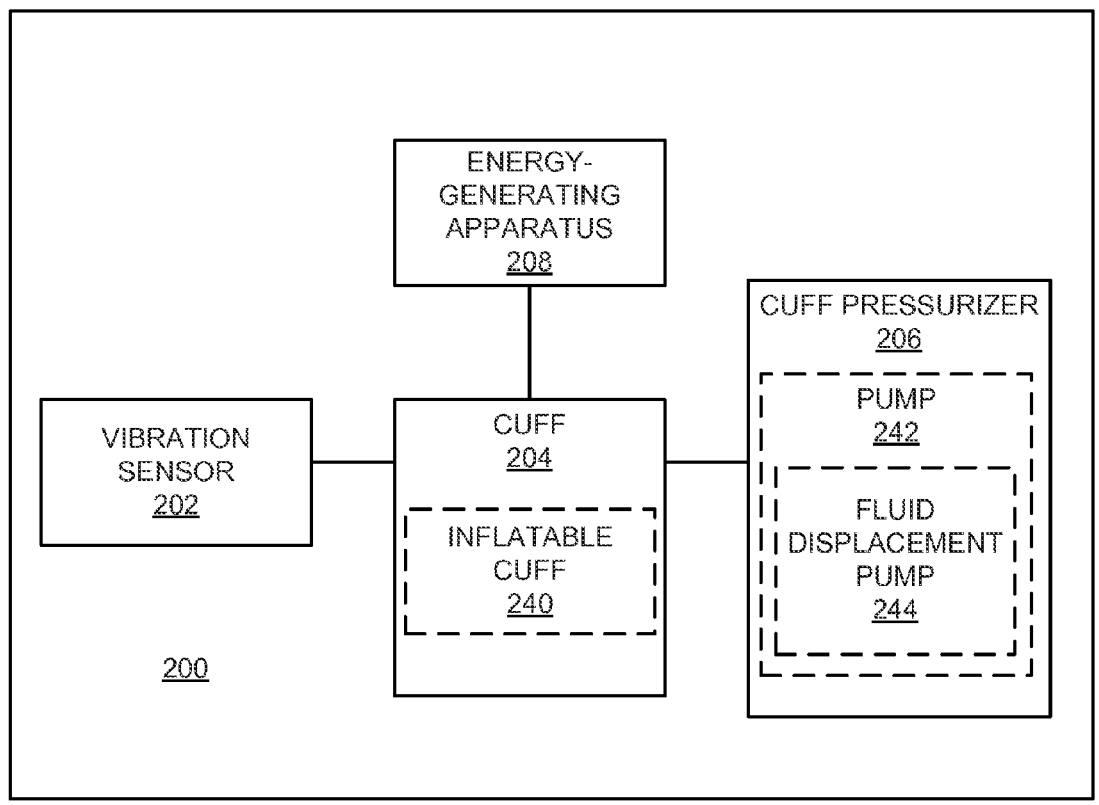
FIG. 22 is a schematic of an alternative embodiment of a blood pressure cuff.

In an embodiment, illustrated in FIG. 22, the blood pressure cuff 200 includes cuff 204 which includes an inflatable cuff 240, which can be inflatable with a gas, a liquid, or a fluid mixture. For example, the inflatable cuff 240 can include a reservoir configured to hold the gas, liquid, or fluid mixture. The reservoir can be constructed of a flexible material such that the reservoir expands upon pressure induced by the gas, liquid, or fluid mixture. Alternatively, the inflatable cuff 240 can include a fixed volume reservoir. The pressure of the fixed volume reservoir can be dictated by a pump or other suitable mechanism. The fixed volume reservoir can include a port through which fluid can flow between the reservoir and the environment or other fluid source. The blood pressure cuff 200 in FIG. 22 also includes cuff pressurizer 206 which includes a pump 242 configured to adjust the fluid pressure of the inflatable cuff 240. The pump 242 can be a fluid displacement pump 244, or other pump suitable to control inflating/deflating the inflatable cuff 240. With the inflatable cuff 240, energy can be recovered by the energy-generating apparatus 208 using internal pressure from the inflatable cuff 240 to do work on the mechanism of the energy-generating apparatus 208 (e.g., one or more of a piezoelectric generator 216, an electromechanical generator 218, a magnetic generator 220, a mechanical generator 222 (with or without spring 224), a turbine 226, a piston 228, and an electroactive polymer 230) as the internal pressure is reduced to ambient pressure. As an example, gas expelled from the cuff can push on a piston, which in turn is linked a generator, can turn a turbine, or the like. Where the mechanical cuff tensioner 232 is employed, energy can be stored as strain mechanically, where relaxation of the mechanical mechanism can apply force to a generator.

Figure 23:
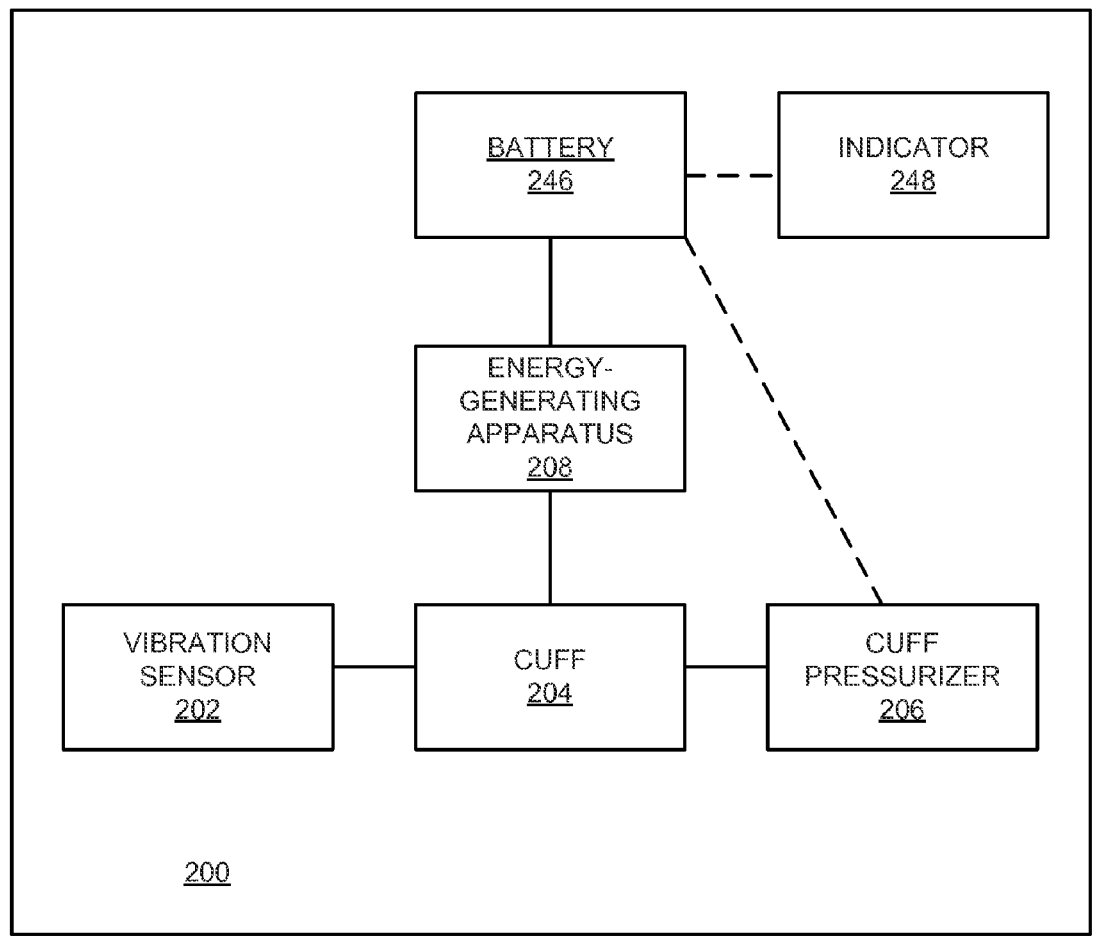
FIG. 23 is a schematic of an alternative embodiment of a blood pressure cuff.

In an embodiment, illustrated in FIG. 23, the blood pressure cuff 200 includes a battery 246 coupled to the energy-generating apparatus 208. The battery 246 can be configured to store the energy generated from the depressurization of the cuff 204 by the energy-generating apparatus 208. For instance, the battery 246 can be operably coupled to the energy-generating apparatus 208, where the energy-generating apparatus 208 can be configured to at least partially recharge the battery 246 with the energy generated from the depressurization of the cuff 204. The battery 246 can be operably coupled to the cuff pressurizer 206 to provide power to the cuff pressurizer. The battery 246 can be configured to provide power to other components of the blood pressure cuff 200, including but not limited to, the vibration sensor 202. The blood pressure cuff 200 can include an indicator 248 operably coupled to the battery 246. The indicator 248 can be configured to indicate that the battery 246 has enough stored energy to provide power to the cuff pressurizer 206 sufficient for performing a blood pressure measurement. The indicator 248 can include a visual indicator (e.g., a light, a display, and the like), an auditory indicator (e.g., an alarm, a buzzer, and the like), or a combination.

Figure 24:
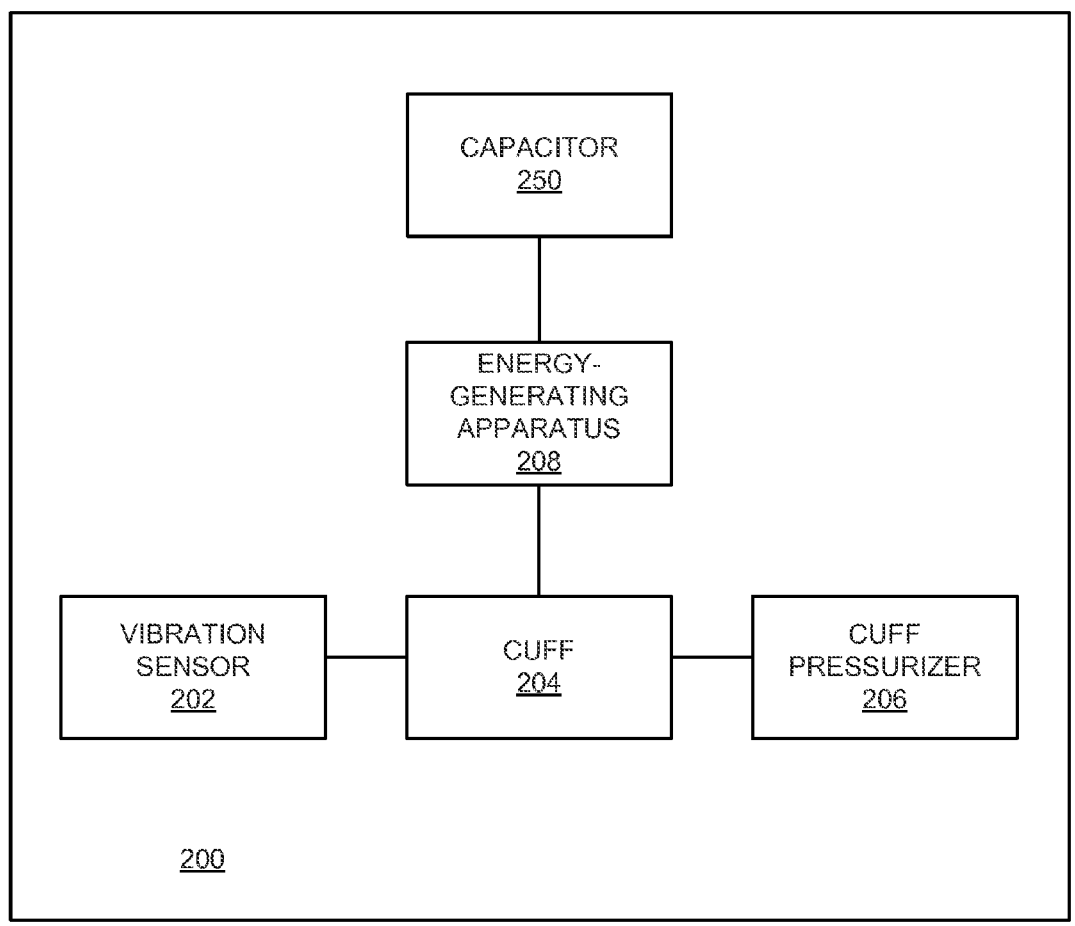
FIG. 24 is a schematic of an alternative embodiment of a blood pressure cuff.

In an embodiment, illustrated in FIG. 24, the blood pressure cuff 200 includes a capacitor 250 coupled to the energy-generating apparatus 208. The capacitor 250 can be configured to buffer the energy generated from the depressurization of the cuff 204 by the energy-generating apparatus 208. For example, the capacitor 250 can be configured to buffer energy generated from the depressurization of the cuff 204, where the energy generated by the energy-generating apparatus 208 may be generated faster than the battery accepts it. The capacitor can also be configured to transduce a variable power profile from cuff relaxation into a uniform profile.

Figure 25:
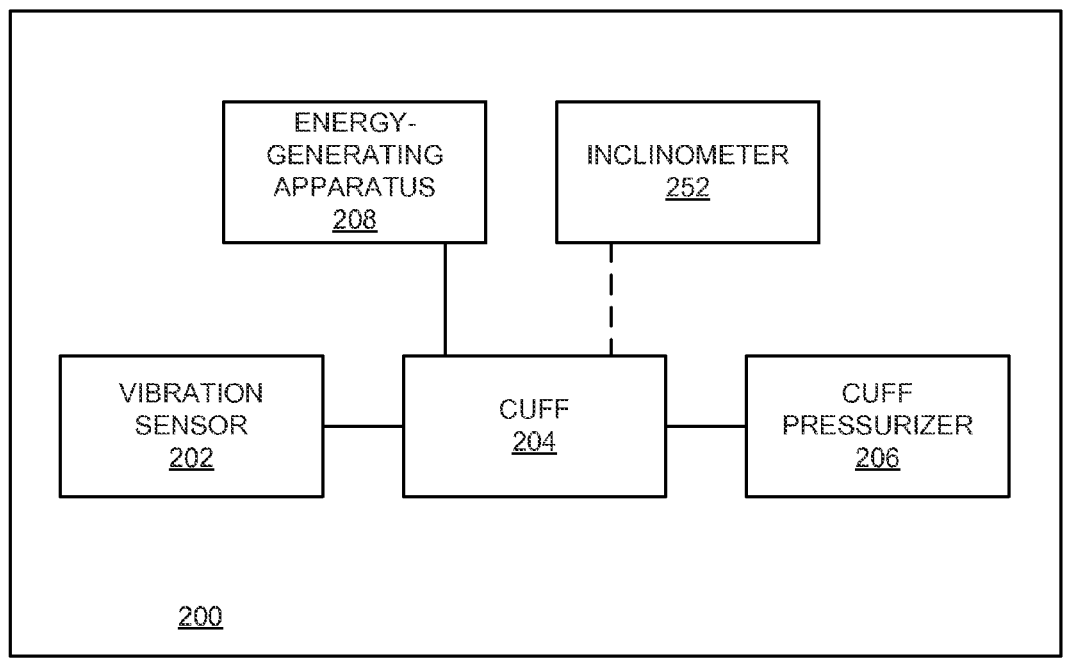
FIG. 25 is a schematic of an alternative embodiment of a blood pressure cuff.
Figure 26:
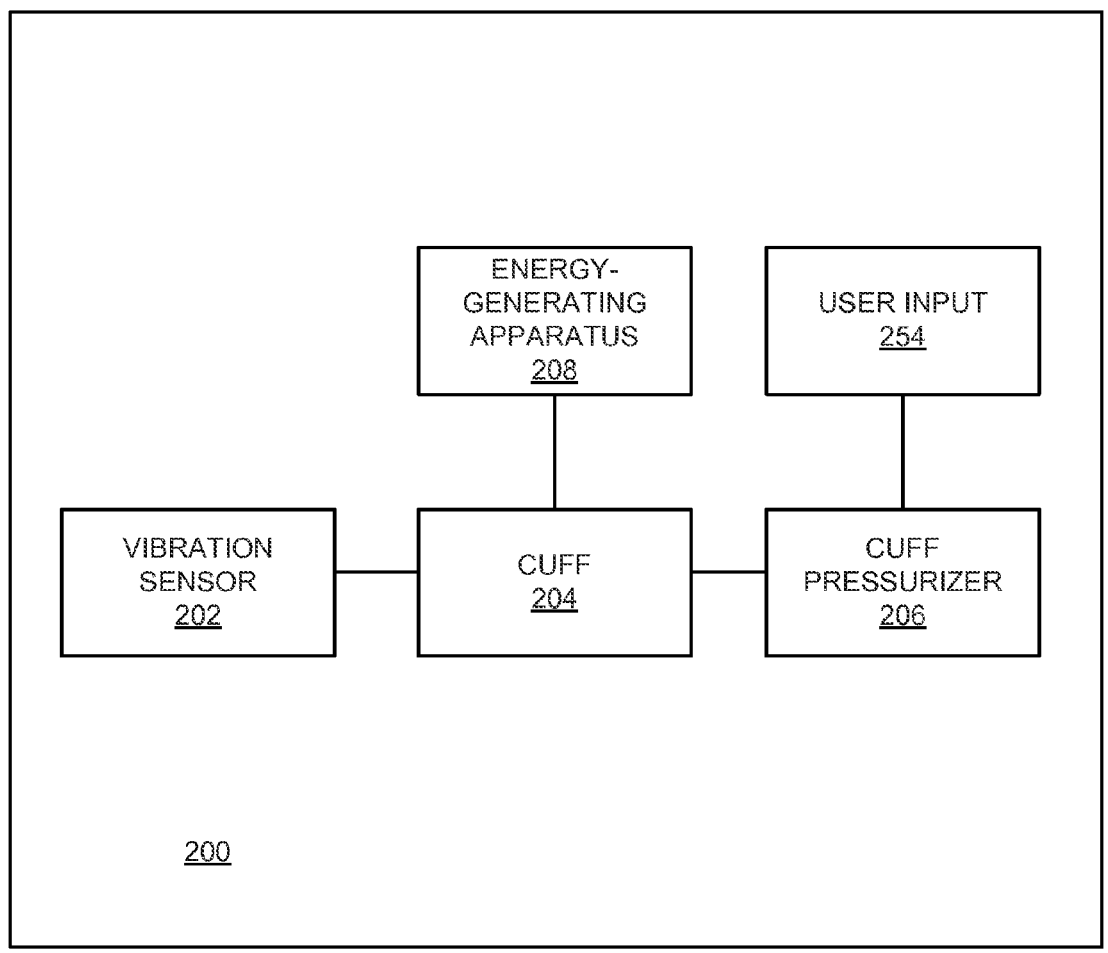
FIG. 26 is a schematic of an alternative embodiment of a blood pressure cuff.

In an embodiment, illustrated in FIG. 25, the blood pressure cuff 200 includes an inclinometer 252 operably coupled to the cuff 204. The inclinometer 252 can be configured to detect an orientation of the cuff 204. The orientation of the cuff 204 can affect the determination of a blood pressure in the lumen by the blood pressure cuff 200. The vibration sensor 202 can be configured to activate when the orientation is detected to be within a specified range. For instance, the specified range can be determined to be a range within which the determination of the blood pressure in the lumen can be made with relatively accurate results (e.g., within a particular standard deviation).

The cuff pressurizer 206 can be configured to activate or deactivate according to one or more of a plurality of methods. For instance, the cuff pressurizer 206 can be configured to adjust the compressive force of the cuff 204 on the lumen according to a scheduled activation. In an embodiment, illustrated in FIG. 26, the blood pressure cuff 200 includes a user input device 254. The cuff pressurizer 206 can be configured to adjust the compressive force of the cuff 204 on the lumen upon a user-given command via the user input device 254. The user-given command can indicate immediate activation, or can be delayed activation, such as through specification of a certain activation time, activation delay, activation schedule, or the like. For instance, the cuff pressurizer 206 can be configured to automatically reduce compressive force applied to the lumen by the cuff 204 upon occurrence of an event, where the event can include a user-given command via the user input device 254.

Figure 27:
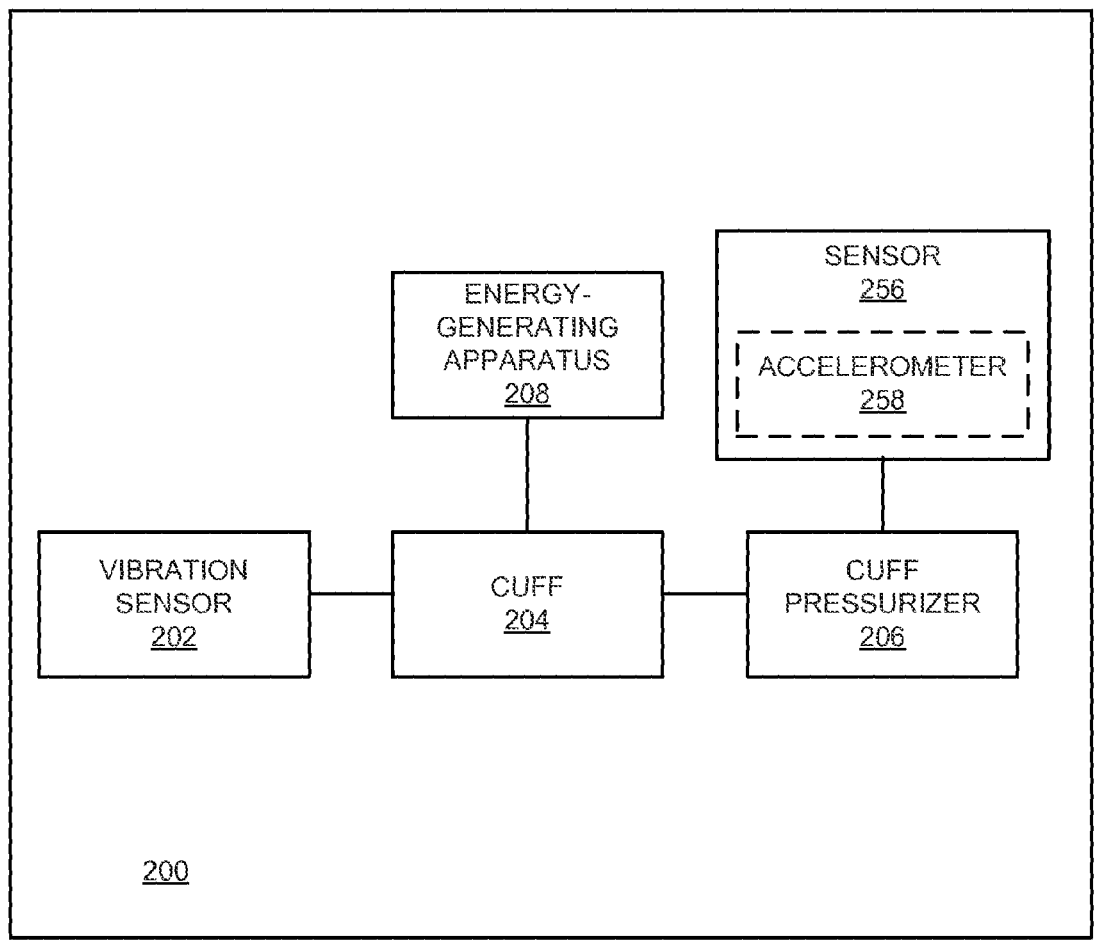
FIG. 27 is a schematic of an alternative embodiment of a blood pressure cuff.

In an embodiment, illustrated in FIG. 27, the blood pressure cuff 200 includes a sensor 256 configured to sense a physiological condition of the human or animal. The sensor 256 can be a sensor suitable to detect a blood oxygenation level, a pulse rate, or other physiological condition. The cuff pressurizer 206 can be configured to adjust the compressive force of the cuff 204 on the lumen upon the sensed physiological condition. The sensed physiological condition can be one or more of a blood oxygenation level and a pulse rate. The sensor 256 can be configured to sense a user activity level, where the cuff pressurizer 206 is configured to adjust the compressive force of the cuff 204 on the lumen upon the user activity level. The user activity level can be one or more of a systemic activity level and a local activity level. The user activity level can include motion of the limb. In an embodiment, the motion of the limb is can be measured by the sensor 256 including an accelerometer 258.

Figure 28:
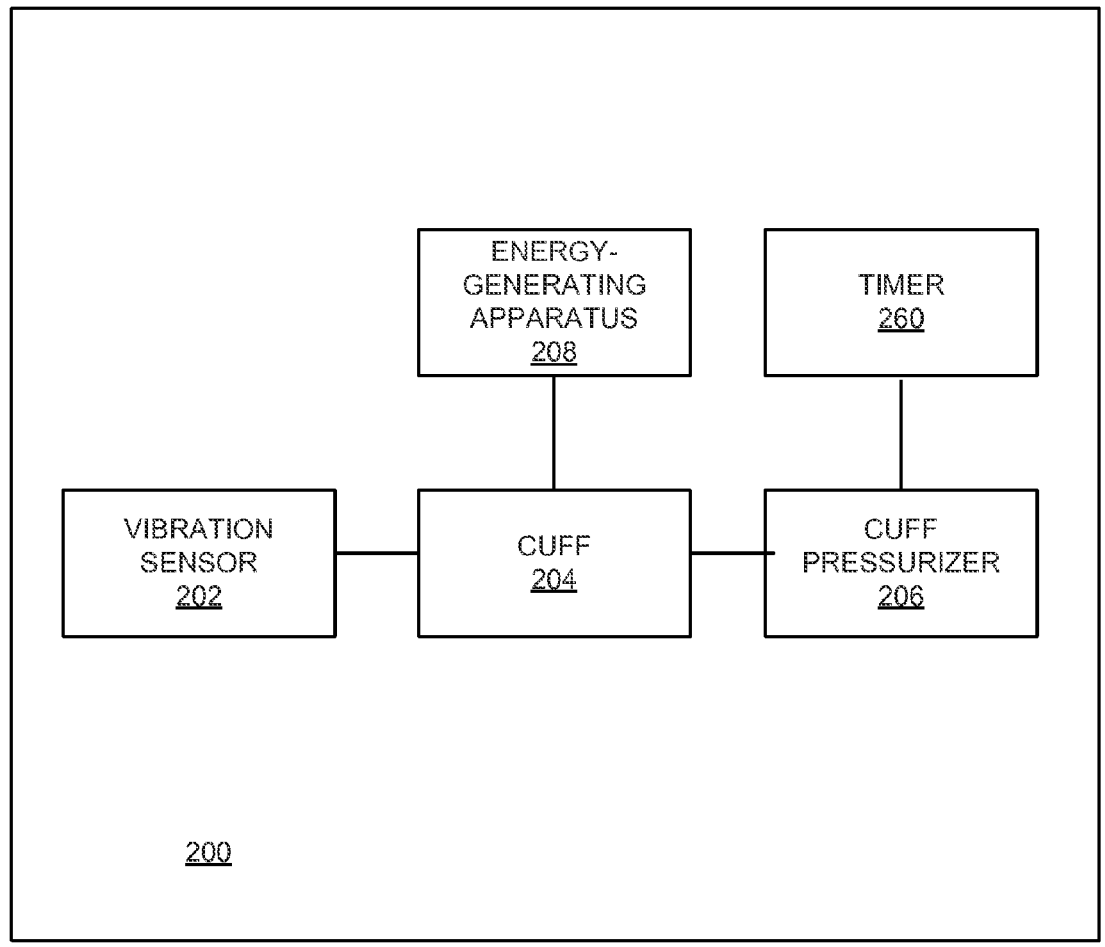
FIG. 28 is a schematic of an alternative embodiment of a blood pressure cuff.

In an embodiment, illustrated in FIG. 28, the blood pressure cuff 200 includes a timer device 260 operably coupled to the cuff pressurizer 206. The timer device 260 can be configured to measure a time-at-tension value of the cuff pressurizer 206. The cuff pressurizer 206 can be configured to automatically reduce compressive force applied to the lumen upon occurrence of an event, wherein the event is exceeding a specified time-at-tension value measured by the timer device 260.

Figure 29:
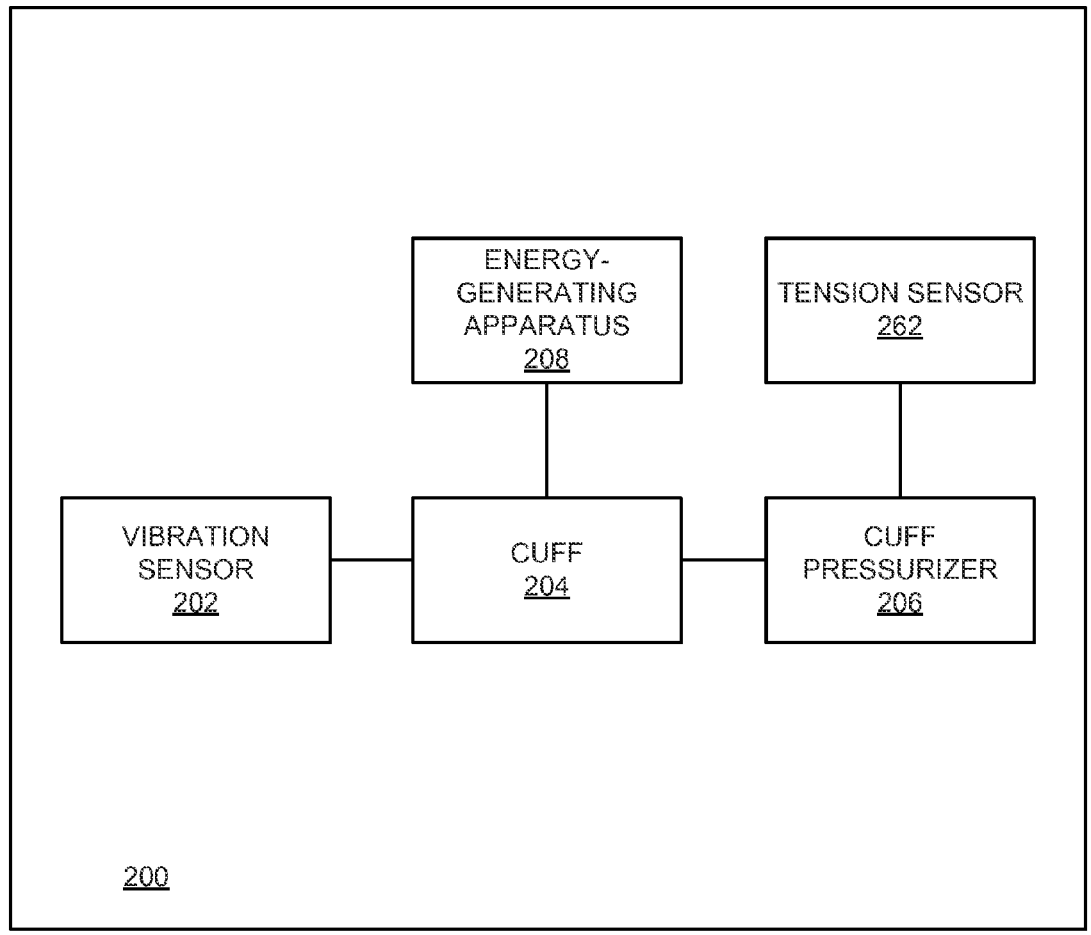
FIG. 29 is a schematic of an alternative embodiment of a blood pressure cuff.

In an embodiment, illustrated in FIG. 29, the blood pressure cuff 200 includes a tension sensor 262 operably coupled to the cuff pressurizer 206. The tension sensor 262 can be configured to measure a tension value of the cuff 204. The cuff pressurizer 206 can be configured to automatically reduce the compressive force applied to the lumen upon occurrence of an event, where the event includes the measured tension value reaching a maximum tension limit. The maximum tension limit can be one or more of a preset limit and a user-specified limit.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. After reading the disclosure herein, it will be appreciated that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, and the vehicle to be utilized is a choice dependent upon the context in which the vehicle will be deployed and the specific concerns (e.g., speed, flexibility, or predictability) of the implementer, any of which can vary. Optical aspects of implementations will typically employ optically-oriented hardware, software, and or firmware.

In some implementations described herein, logic and similar implementations can include software or other control structures.

Electronic circuitry, for example, can have one or more paths of electrical current constructed and arranged to implement various functions as described herein. In some implementations, one or more media can be configured to bear a device-detectable implementation when such media hold or transmit a device detectable instruction operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations can include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, implementations can be provided, in whole or in part, by source code, such as C++, or other code sequences. In other implementations, source or other code implementation, using commercially available and/or techniques in the art, can be compiled/implemented/translated/converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) can be manifested as a Verilog-type hardware description (e.g., via Hardware Description Language (HDL) and/or Very High Speed Integrated Circuit Hardware Descriptor Language (VHDL)) or other circuitry model which can then be used to create a physical implementation having hardware (e.g., an Application Specific Integrated Circuit).

The herein-described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Such terms (e.g. "configured to") can generally encompass active-state components and/or inactive-state components and/or standby-state components, unless context requires otherwise.

While particular aspects of the present subject matter described herein have been shown and described, it will be apparent that changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, recited operations therein can generally be performed in any order. Also, although various operational flows are presented in a sequence(s), it should be understood that the various operations can be performed in other orders than those which are illustrated, or can be performed concurrently. Examples of such alternate orderings can include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent. The various aspects and embodiments disclosed herein are for purposes of illustration and are not intended to be limiting, with the true scope and spirit being indicated by the following claims.

What is claimed is:

1. A device, comprising:
   a vibration sensor configured to sense blood flow in a lumen of a person;
   a cuff coupled to the vibration sensor and configured to contact a limb of the person;
   a mechanical cuff tensioner coupled to the cuff, the mechanical cuff tensioner configured to adjust a compressive force of the cuff on the lumen;
   a tension sensor operably coupled to the mechanical cuff tensioner, the tension sensor configured to measure a first tension value of the cuff during a first sense by the vibration sensor and to measure a second tension value of the cuff during a second sense by the vibration sensor;
   a recorder mechanism configured to record the first tension value, a first measurement by the vibration sensor, the second tension value, and a second measurement by the vibration sensor; and
   an energy-recovery mechanism configured to recover energy from activation of the mechanical cuff tensioner to reduce the compressive force of the cuff on the lumen.

2. The device of claim 1, wherein the vibration sensor includes an acoustic sensor.

3. The device of claim 2, further comprising:
   a controller operably coupled to the acoustic sensor, the controller including circuitry to determine a Korotkoff sound indicative of at least one systole and diastole based on at least one of the first measurement or the second measurement.

4. The device of claim 1, wherein the vibration sensor includes a piezoelectric sensor.

5. The device of claim 4, further comprising:
   a controller operably coupled to the piezoelectric sensor, the controller including circuitry to determine at least one vibration pattern indicative of systole and diastole based on at least one of the first measurement or the second measurement.

6. The device of claim 1, wherein the first measurement by the vibration sensor is at a systolic phase of the blood flow, and wherein the second measurement by the vibration sensor is at a diastolic phase of the blood flow.

7. The device of claim 1, wherein the tension sensor is configured to halt adjustment of the compressive force of the cuff on the lumen by the mechanical cuff tensioner at a designated pressure.

8. The device of claim 7, wherein the designated pressure is a pressure suitable for the vibration sensor to sense blood flow in the lumen.

9. The device of claim 1, further comprising:
   a contact sensor operably coupled to the cuff, the contact sensor configured to determine contact between the limb and a torso of the person.

10. The device of claim 1, further comprising:
    a controller operably coupled to the recorder mechanism, the controller configured to determine a blood pressure value based on the first tension value, the second tension value, the first measurement by the vibration sensor, and the second measurement by the vibration sensor.

11. The device of claim 10, wherein the recorder mechanism is configured to record the determined blood pressure value.

12. The device of claim 11, further comprising:
a relay mechanism operably coupled to the recorder mechanism, the relay mechanism configured to relay the determined blood pressure value to a healthcare provider.

13. The device of claim 12, wherein the relay mechanism is at least one of (i) configured to immediately relay the determined blood pressure value when the determined blood pressure value is at least one of above a threshold value, below the threshold value, or irregular or (ii) configured to relay, according to a schedule, the determined blood pressure value when the determined blood pressure value is within a normal range.

14. The device of claim 10, wherein the controller is at least one of (i) configured to identify the determined blood pressure value as being at least one of above a threshold value, below the threshold value, or at the threshold value or (ii) configured to generate an alert based upon the determined blood pressure value.

15. The device of claim 11, wherein the vibration sensor is configured to measure a pulse rate.

16. The device of claim 15, wherein the recorder mechanism is configured to record the measured pulse rate.

17. The device of claim 16, further comprising:
a relay mechanism operably coupled to the recorder mechanism, the relay mechanism configured to relay the measured pulse rate to a healthcare provider.

18. The device of claim 17, wherein the relay mechanism is at least one of (i) configured to immediately relay the measured pulse rate when the measured pulse rate is at least one of above a threshold value, below the threshold value, or irregular or (ii) configured to relay, according to a schedule, the measured pulse rate when the measured pulse rate is within a normal range.

19. The device of claim 15, further comprising:
a controller operably coupled to the recorder mechanism, the controller configured to identify the measured pulse rate as being at least one of above a threshold value, below the threshold value, or at the threshold value, wherein the controller is configured to generate an alert based upon the measured pulse rate.

20. The device of claim 1, wherein the vibration sensor is configured to measure a pulse structure.

21. The device of claim 20, wherein the recorder mechanism is configured to record the measured pulse structure.

22. The device of claim 21, further comprising:
a relay mechanism operably coupled to the recorder mechanism, the relay mechanism configured to relay the measured pulse structure to a healthcare provider.

23. The device of claim 22, wherein the relay mechanism is at least one of (i) configured to immediately relay the measured pulse structure when the measured pulse structure is at least one of above a threshold value, below the threshold value, or irregular or (ii) configured to relay, according to a schedule, the measured pulse structure when the measured pulse structure is within a normal range.

24. The device of claim 20, further comprising:
a controller operably coupled to the recorder mechanism, the controller configured to identify the measured pulse structure as being at least one of above a threshold value, below the threshold value, or at the threshold value, wherein the controller is configured to generate an alert based upon the measured pulse structure.

25. The device of claim 1, wherein the mechanical cuff tensioner is configured to adjust the compressive force of the cuff on the lumen according to a scheduled activation.

26. The device of claim 1, further comprising:
a user input device, wherein the mechanical cuff tensioner is configured to adjust the compressive force of the cuff on the lumen upon a user-given command via the user input device.

27. The device of claim 1, further comprising:
a sensor configured to sense a physiological condition of the person, wherein the mechanical cuff tensioner is configured to adjust the compressive force of the cuff on the lumen upon the sensed physiological condition.

28. The device of claim 27, wherein the sensed physiological condition includes at least one of a blood oxygenation level or a pulse rate.

29. The device of claim 1, further comprising:
a sensor configured to sense a user activity level, wherein the mechanical cuff tensioner is configured to adjust the compressive force of the cuff on the lumen upon the user activity level.

30. The device of claim 29, wherein the user activity level includes at least one of a systemic activity level or a local activity level.

31. The device of claim 29, wherein the sensor includes an accelerometer configured to measure a motion of the limb, and wherein the user activity level includes the motion of the limb.

32. The device of claim 1, wherein the mechanical cuff tensioner is configured to automatically reduce compressive force applied to the lumen upon occurrence of an event.

33. The device of claim 32, wherein the event is a tension value measured by the tension sensor reaching a maximum tension limit.

34. The device of claim 33, wherein the maximum tension limit is at least one of a preset limit or a user-specified limit.

35. The device of claim 32, further comprising:
at least one of (i) a user input device, wherein the event is a user-given command via the user input device or (ii) a timer device operably coupled to the mechanical cuff tensioner, the timer device configured to measure a time-at-tension value of the mechanical cuff tensioner, wherein the event is exceeding a specified time-at-tension value.

36. The device of claim 1, wherein the limb includes at least one of an arm, a finger, a leg, or a toe.

37. The device of claim 1, wherein a length of the cuff is configured to extend partially around the limb, and wherein the cuff includes a first end and a second end, the cuff defining a gap between the first end and the second end.

38. The device of claim 1, further comprising:
a controller configured to calculate at least one of a systolic blood pressure or a diastolic blood pressure based on the first tension value, the second tension value, and at least one of a circumference of the cuff, a lateral dimension of the cuff, or an eccentricity factor of the cuff.

39. The device of claim 1, further comprising:
a power source operably coupled to at least one of the vibration sensor, the tension sensor, or the mechanical cuff tensioner.

40. The device of claim 1, wherein the mechanical cuff tensioner includes at least one of (i) an electroactive polymer or (ii) a flexible member attached to a rotatable member.

41. The device of claim 40, wherein the mechanical cuff tensioner includes the flexible member attached to the rotatable member, and wherein the flexible member is configured to wind around the rotatable member to tighten the cuff and to unwind around the rotatable member to loosen the cuff.

42. The device of claim 1, further comprising:
at least one of (i) a battery coupled to the energy-recovery mechanism and configured to store the recovered energy or (ii) a capacitor coupled to the energy-recovery mechanism and configured to buffer the recovered energy.

43. The device of claim 1, wherein the mechanical cuff tensioner is at least one of mechanically powered or battery powered.

44. The device of claim 1, wherein the mechanical cuff tensioner includes a connector mechanism configured to position a first end the cuff in proximity to a second end of the cuff, and wherein the connector mechanism is configured to adjust the compressive force of the cuff on the lumen by adjusting the position of the first end of the cuff relative to the position of the second end of the cuff.

45. The device of claim 44, wherein the connector mechanism includes at least one of a lever or a motor.

46. The device of claim 1, wherein the mechanical cuff tensioner includes a connector mechanism configured to overlap at least a portion of the cuff, and wherein the connector mechanism is configured to adjust the compressive force of the cuff on the lumen by adjusting the overlap.

47. The device of claim 46, wherein the connector mechanism includes at least one of a lever or a motor.

48. The device of claim 1, further comprising:
a motion sensor operably coupled to the recorder mechanism, the motion sensor configured to detect a motion of the cuff, wherein the motion sensor includes circuitry that disables the mechanical cuff tensioner when the motion exceeds a threshold or disables the tension sensor when the motion exceeds a threshold.

49. The device of claim 1, further comprising:
an inclinometer operably coupled to the cuff, the inclinometer configured to detect an orientation of the cuff, wherein the vibration sensor is configured to activate when the orientation is within a specified range.

50. The device of claim 49, further comprising:
a controller configured to determine a correction factor based upon the orientation.

* * * * *